United States Patent
Weber et al.

(10) Patent No.: US 7,163,655 B2
(45) Date of Patent: Jan. 16, 2007

(54) METHOD AND APPARATUS FOR EXTRUDING POLYMERS EMPLOYING MICROWAVE ENERGY

(75) Inventors: Jan Weber, Maple Groove, MN (US); Scott Schewe, Eden Prairie, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 267 days.

(21) Appl. No.: 10/347,005

(22) Filed: Jan. 17, 2003

(65) Prior Publication Data

US 2003/0183972 A1 Oct. 2, 2003

Related U.S. Application Data

(63) Continuation-in-part of application No. 10/212,926, filed on Aug. 6, 2002, which is a continuation-in-part of application No. 10/109,220, filed on Mar. 28, 2002.

(51) Int. Cl.
| | |
|---|---|
| *H05B 6/78* | (2006.01) |
| *H05B 6/64* | (2006.01) |
| *B29C 43/30* | (2006.01) |
| *B29C 43/26* | (2006.01) |
| *B29C 47/06* | (2006.01) |
| *B29C 47/24* | (2006.01) |
| *A61M 25/10* | (2006.01) |
| *A61M 25/16* | (2006.01) |
| *B29C 61/06* | (2006.01) |

(52) U.S. Cl. ............... 264/474; 264/489; 264/515; 264/146; 264/75; 219/679

(58) Field of Classification Search ............ 264/75, 264/146, 515, 432, 489, 474; 604/103.01; 219/678, 679, 693, 762, 756

See application file for complete search history.

(56) References Cited

U.S. PATENT DOCUMENTS 2,863,174 A 12/1958 Schuman et al.

(Continued)

FOREIGN PATENT DOCUMENTS

EP 0 355 423 2/1990

(Continued)

OTHER PUBLICATIONS

Pages from Barlow's Scientific Glassblowing Inc's website.
U.S. Appl. No. 10/375,719, filed Feb. 25, 2003, John Chen.

(Continued)

*Primary Examiner*—Christina Johnson
*Assistant Examiner*—Matthew J. Daniels
(74) *Attorney, Agent, or Firm*—Miller Matthias & Hull

(57) ABSTRACT

An apparatus and method for molding balloon catheters is disclosed. The balloon may be molded by providing a polymeric tube within a mold having an interior cavity in the shape of the desired balloon. Microwave energy, which may be generated by a gyrotron, may then be directed toward the mold, to heat the polymeric material without heating the mold. Once heated, pressurized fluid may be injected into the tube to blow the polymeric material against the interior cavity whereupon the material can cool to form the balloon or can be further heatset by additional microwave energy and be cooled to form the balloon. In accordance with one embodiment, microwave energy can also be used without a mold to form a medical device. A polymer extrusion apparatus is disclosed utilizing a microwave energy for heating polymer feedstock material within the extruder tip and die unit just prior to formation of the extrudate product. A cooling bath mechanism, which in one embodiment can also include a cooling tube member having a cooling medium forced therethrough, is also disclosed. An apparatus for preparing polymer disk members, to use as the polymer feedstock material for the microwave extrusion apparatus, is also disclosed. Apparatus for interconnecting and rotating the polymer disk members, the die tip, or the die, or any combination thereof, for creating angularity characteristics in the polymer extrudate, is also disclosed.

27 Claims, 20 Drawing Sheets

U.S. PATENT DOCUMENTS

| | | | | |
|---|---|---|---|---|
| 3,483,597 | A * | 12/1969 | Singalewitch et al. | 425/378.1 |
| 3,620,876 | A | 11/1971 | Guglielmo, Sr., et al. | |
| 3,874,207 | A | 4/1975 | Lemelson | |
| 3,957,943 | A | 5/1976 | Ogura | |
| 3,993,529 | A | 11/1976 | Farkas | |
| 4,003,554 | A | 1/1977 | Chaufforeaux | |
| 4,035,547 | A | 7/1977 | Heller, Jr. et al. | |
| 4,035,598 | A | 7/1977 | Van Amsterdam | |
| 4,040,162 | A | 8/1977 | Isogai et al. | |
| 4,093,484 | A * | 6/1978 | Harrison et al. | 156/244.13 |
| 4,143,112 | A | 3/1979 | Turner | |
| 4,298,324 | A | 11/1981 | Soulier | |
| 4,339,295 | A * | 7/1982 | Boretos et al. | 156/275.7 |
| 4,390,482 | A | 6/1983 | Feurer | |
| 4,407,651 | A | 10/1983 | Beck et al. | |
| 4,454,234 | A | 6/1984 | Czerlinski | |
| 4,483,341 | A | 11/1984 | Witteles | |
| 4,568,262 | A | 2/1986 | Feurer | |
| 4,671,757 | A | 6/1987 | Volk, Jr. | |
| 4,672,972 | A | 6/1987 | Berke | |
| 4,760,228 | A * | 7/1988 | Kudo | 219/686 |
| 4,764,394 | A | 8/1988 | Conrad | |
| 4,806,086 | A * | 2/1989 | Bloch et al. | 425/114 |
| 4,820,466 | A * | 4/1989 | Zachariades | 264/119 |
| 4,859,380 | A | 8/1989 | Ogata | |
| 4,860,744 | A | 8/1989 | Johnson et al. | |
| 4,930,494 | A | 6/1990 | Takehana et al. | |
| 4,950,239 | A | 8/1990 | Gahara et al. | |
| 4,977,886 | A | 12/1990 | Takehana et al. | |
| 4,989,608 | A | 2/1991 | Ratner | |
| 5,104,593 | A | 4/1992 | Joseph | |
| 5,154,179 | A | 10/1992 | Ratner | |
| 5,156,785 | A * | 10/1992 | Zdrahala | D12/187 |
| 5,172,551 | A | 12/1992 | Nakajima et al. | |
| 5,207,227 | A | 5/1993 | Powers | |
| 5,222,543 | A | 6/1993 | Carlstrom et al. | |
| 5,258,160 | A * | 11/1993 | Utsumi et al. | 264/558 |
| 5,290,266 | A | 3/1994 | Rohling et al. | |
| 5,296,272 | A | 3/1994 | Matossian et al. | |
| 5,324,345 | A * | 6/1994 | Rutjes et al. | 65/64 |
| 5,330,742 | A | 7/1994 | Deutsch et al. | |
| 5,352,871 | A | 10/1994 | Ross et al. | |
| 5,411,730 | A | 5/1995 | Kirpotin et al. | |
| 5,429,583 | A | 7/1995 | Paulus et al. | |
| 5,433,717 | A | 7/1995 | Rubinsky et al. | |
| 5,470,423 | A * | 11/1995 | Hawley et al. | 156/166 |
| 5,496,311 | A | 3/1996 | Abele et al. | |
| 5,514,379 | A | 5/1996 | Weissleder et al. | |
| 5,599,492 | A * | 2/1997 | Engelson | 264/167 |
| 5,609,624 | A * | 3/1997 | Kalis | 623/1.32 |
| 5,622,665 | A | 4/1997 | Wang | |
| 5,628,950 | A | 5/1997 | Schrenk et al. | |
| 5,641,423 | A | 6/1997 | Bridges et al. | |
| 5,653,778 | A | 8/1997 | Rutjes et al. | |
| 5,690,109 | A | 11/1997 | Govind et al. | |
| 5,693,376 | A | 12/1997 | Fetherston et al. | |
| 5,706,810 | A | 1/1998 | Rubinsky et al. | |
| 5,720,939 | A | 2/1998 | Schroder | |
| 5,728,079 | A | 3/1998 | Weber et al. | |
| 5,744,958 | A | 4/1998 | Werne | |
| 5,746,701 | A * | 5/1998 | Noone | 600/585 |
| 5,762,741 | A | 6/1998 | Kodokian | |
| 5,762,972 | A | 6/1998 | Byon | |
| 5,773,042 | A | 6/1998 | Amano et al. | |
| 5,775,338 | A | 7/1998 | Hastings | |
| 5,787,959 | A | 8/1998 | Lamanan et al. | |
| 5,817,017 | A | 10/1998 | Young et al. | |
| 5,844,217 | A | 12/1998 | Hawley et al. | |
| 5,855,553 | A | 1/1999 | Tajima et al. | |
| 5,908,410 | A | 6/1999 | Weber et al. | |
| 5,948,194 | A | 9/1999 | Hill et al. | |
| 5,951,513 | A | 9/1999 | Miraki | |
| 6,004,289 | A | 12/1999 | Saab | |
| 6,035,657 | A | 3/2000 | Dobak, III et al. | |
| 6,040,019 | A | 3/2000 | Ishida et al. | |
| 6,056,844 | A | 5/2000 | Guiles et al. | |
| 6,061,587 | A | 5/2000 | Kucharczyk et al. | |
| 6,106,263 | A * | 8/2000 | Schmid et al. | 425/144 |
| 6,123,920 | A | 9/2000 | Gunther et al. | |
| 6,137,093 | A | 10/2000 | Johnson, Jr. | |
| 6,176,857 | B1 | 1/2001 | Ashley | |
| 6,190,355 | B1 | 2/2001 | Hastings | |
| 6,203,777 | B1 | 3/2001 | Schroder | |
| 6,207,134 | B1 | 3/2001 | Fahlvik et al. | |
| 6,224,536 | B1 | 5/2001 | Pike | |
| 6,231,516 | B1 | 5/2001 | Keilman et al. | |
| 6,248,196 | B1 | 6/2001 | Waitz et al. | |
| 6,270,707 | B1 | 8/2001 | Hori et al. | |
| 6,270,711 | B1 | 8/2001 | Gellert et al. | |
| 6,272,370 | B1 | 8/2001 | Gillies et al. | |
| 6,280,384 | B1 | 8/2001 | Loeffler | |
| 6,352,779 | B1 | 3/2002 | Edwards et al. | |
| 6,361,759 | B1 | 3/2002 | Frayne et al. | |
| 6,368,994 | B1 | 4/2002 | Sklyarevich | |
| 6,418,337 | B1 | 7/2002 | Torchia et al. | |
| 6,478,911 | B1 | 11/2002 | Wang et al. | |
| 6,696,121 | B1 | 2/2004 | Jung, Jr. et al. | |
| 2001/0043998 | A1 | 11/2001 | Chen et al. | |
| 2001/0054775 | A1 | 12/2001 | Nandu et al. | |
| 2002/0010489 | A1 * | 1/2002 | Grayzel et al. | 606/194 |
| 2002/0095198 | A1 | 7/2002 | Whitebook et al. | |
| 2003/0055449 | A1 | 3/2003 | Lee et al. | |

FOREIGN PATENT DOCUMENTS

| | | | |
|---|---|---|---|
| EP | 0 525 069 B1 | | 3/1996 |
| JP | 2001 314390 | | 11/2001 |
| WO | WO 80/02124 | | 10/1980 |
| WO | WO 89/11874 | | 12/1989 |
| WO | WO 99/03306 | | 1/1999 |
| WO | WO 01/51115 | * | 1/2000 |
| WO | WO 00/64608 | | 11/2000 |
| WO | WO 01/51115 | | 7/2001 |
| WO | WO 03/035161 | | 5/2003 |

OTHER PUBLICATIONS

Ashley, S., assoc. ed., "Electric Plastics," *Mechanical Engineering*, Apr. 1998, http://www.memagazine.org/backissues/apri98/features/plastics/plastics.html (Jul. 3, 2003).

Ballinger, J.R., "MRI Contrast Agents," *MRI Tutor Web Site*, http://www.mritutor.org/mritutor/contrast.html (Aug. 8, 2002).

Ballinger, J.R. "Introduction to MRI," *MRI Tutor Web Site*, http://www.mritutor.org/mritutor/index.html (Jul. 3, 2003).

Bowman, M., "The Big Chill," http://www.ameslab.gov/News/Inquiry/fall97/bigchill.html (Aug. 8, 2002).

EXPLORATORIUM, "Curie Point," http://www.exploratorium.edu/snacks/curie_point.html (Jul. 3, 2003).

EXPLORATORIUM, "Curie Temperature," Abstract from http://www.exploratorium.edu/serf/phenomena/curie_temperature.html (Aug. 8, 2002).

Gavrin, "What is Physics Good For?", IUPUI, http://webphysics.iupui.edu/251/251Sp97GFApr28.html (Aug 8, 2002).

Gould, T.A., "How MRI Works," http://www.howstuffworks.com/mri.htm (Aug. 8, 2002).

Gould, T.A., "How MRI Works," http://electronics.howstuffworks.com/mri.htm/printable (Jul. 3, 2003).

Hesselink, J.R., "Basic Principles Of MR Imaging," http://spinwarp.ucsd.edu/NeuroWeb/Test/br-100.htm (Jul. 3, 2003).

Hornak, J.P., *The Basics Of MRI*, http://www.cis.rit.edu/htbooks/mri/chap-1/chap-1.htm, Chapters 1 and 3 (Jan. 4, 2002).

Hornak, J.P., *The Basics Of MRI*, http://www.cis.rit.edu/htbooks/mri, Chapters 1, 2, 6, 8 and 9 (Jul. 3, 2003).

International Search Report PCT US 03/09494, report mailed Jun. 9, 2003.

King, M.M., "Module #2: Basic Principles Of MRI," http://www.erads.com/mrimod.htm (Aug. 8, 2002).

Koehler, K.R., "Body Temperature Regulation," http://www.rwc.uc.edu/Koehler/biophys/8d.html (Jul. 8, 2003).

Konings, et al., "Heating Around Intravascular Guidewires By Resonating RF Waves," Abstract from *J. Magn. Reson. Imaging*, 12(1):79-85 (2000).

Kuperman, V., *Magnetic Resonance Imaging: Physical Principles And Applications*, Academic Press (2000).

"Laboratory #27: Peltier Elements And Thermistors," Indiana University Dept. of Physics Intermediate Physics Laboratory (P309), http://www.physics.indiana.edu/~dmckinne/p309/ (last modified Nov. 2, 2000).

Ladd, et al., "Reduction Of Resonant RF Heating In Intravascular Catheters Using Coaxial Chokes," Abstract from *Magn. Reson. Med.*, 43(4):615-619 (2000).

Liu, et al., "Safety Of MRI-Guided Endovascular Guidewire Applications," Abstract from *J. Magn. Reson. Imaging*, 12(1):75-78 (2000).

"Magnetism," xrefer, http://www.xrefer.com/entry/489951 (Aug. 8, 2002).

"The Mean Field Model," http://carini.physics.indiana.edu/P616/lecture-notes/mean-field.html (Aug. 8, 2002).

"The Mean Field Model," http://carini.physics.indiana.edu/P616/lecture-notes/mean-field.html (Jul. 3, 2003).

Nitz, et al., "On The Heating Of Linear Conductive Structures As Guide Wires And Catheters In Interventional MRI," Abstract from *J. Magn. Reson. Imaging*, 13(10):105-114 (2001).

"The Nobel Prize In Chemistry 2000," http://www.nobel.se/chemistry/laureates/2000/index.html (Jul. 3, 2003).

"Nobel Prize 2000 For The Discovery And Development Of Conductive Polymers," Panipol Conductive Polymers, Panipol Ltd., http://www.panipol.com/ (Jul. 8, 2003).

"About Technology, Definitions, Advantages, Products, Applications, Evaluation, Techn. History, Contact, References," Panipol Conductive Polymers, Panipol Ltd., http://www.panipol.com/noframes.htm (Jul. 3, 2003).

"The Heatsink Guide: Peltier Coolers," http://www.heatsink-guide.com/peltier.htm (Jul. 3, 2003).

Pierce, J. P., Abstract, Table of Contents, and Chapter 1: "Introduction to Magnetic Nanostructures" in "Tailored Magnetic Nanostructures on Surfaces," available at http://web.utk.edu/~jp/thesisJP.htm, May 2003.

Stephens, J., "Peltier CPU Cooling," http://www.pcmech.com/show/processors/140/ (Aug. 13, 2002).

Tellurex Corporation, "Frequently Asked Questions," http://www.tellurex.com/resource/txfaqc.htm (Sep. 16, 2002).

"'TMD' System Overview," Otari, Inc., http://www.otari.com/products/TMD.html (Aug. 8, 2002).

"Types Of Magnetism," http://www.physics.hull.ac.uk/magnetics/Magnetism/Types/types.html (Aug. 8, 2002).

"Types Of Magnetism," http://www.physics.hull.ac.uk/magnetics/Magnetism/Types/types.html (Jul. 3, 2003).

Wohlgemuth, et al., "Laser-Induced Interstitial Thermotherapy Of The Uterus In An Open MRI System: Preliminary In Vitro And In Vivo Experience," http://www.toshiba-medical.co.jp/tmd/review/rv76/r76_6.thm (Jul. 8, 2003).

Pages from Farlow's Scientific Glassblowing Inc.'s website.

International Search Report; PCT US 03/01203, reported dated Jun. 4, 2003.

\* cited by examiner

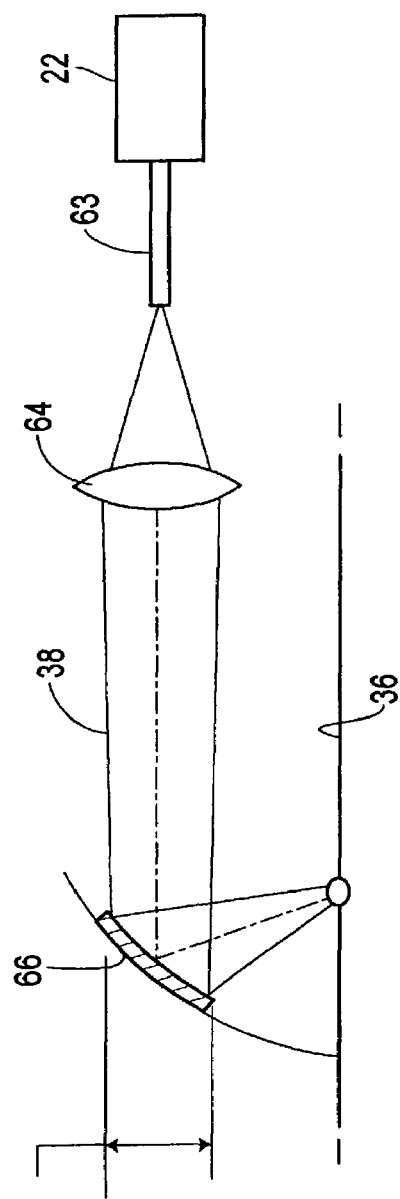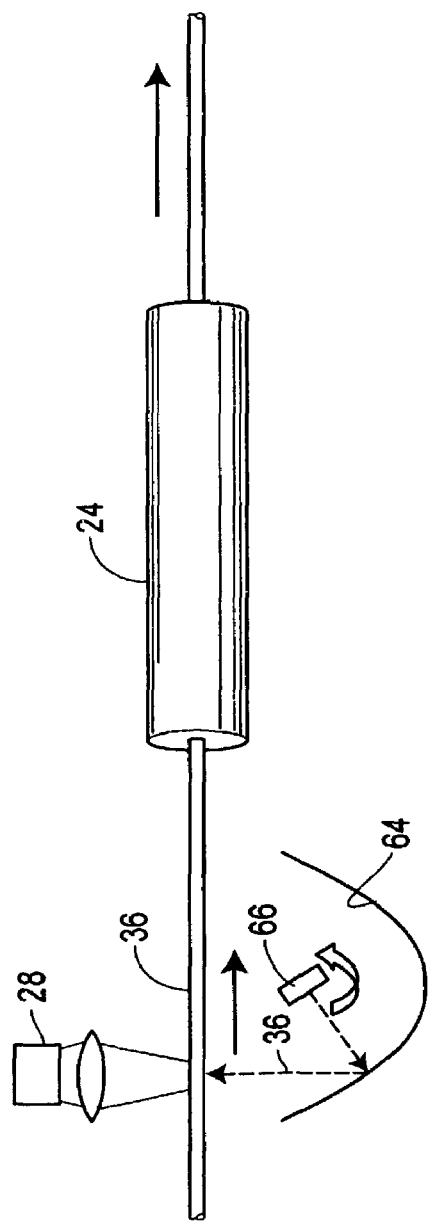
FIG. 4
FIG. 5

METHOD AND APPARATUS FOR EXTRUDING POLYMERS EMPLOYING MICROWAVE ENERGY

CROSS REFERENCE TO RELATED APPLICATION

This application is a continuation-in-part of U.S. patent application Ser. No. 10/212,926, filed on Aug. 6, 2002, which in turn is a continuation-in-part of U.S. patent application Ser. No. 10/109,220, filed on Mar. 28, 2002.

FIELD OF THE DISCLOSURE

The disclosure generally relates to extruded medical devices and, more particularly, relates to methods of manufacturing extruded medical devices, including with use of microwave energy, and for use in the field of angiography.

BACKGROUND OF THE DISCLOSURE

Angioplasty is an effective medical procedure performed to expand constricted sections of blood vessels. In such a procedure, an angioplasty balloon or balloon catheter is navigated to the site of the constriction. The balloon is inflated after reaching the site, by way of fluid pressure injected into the balloon, to thereby expand its dimension. The expansion of the balloon exerts pressure on the vessel walls to thereby widen the vessel and alleviate constriction to blood flow.

Conventionally, such balloons are manufactured from a polymeric material and are molded in a blow molding procedure. More specifically, a cylinder or tube of polymeric material, known as a parison, is placed within a mold having an interior cavity in the desired shape of the balloon. The mold is then heated, with the heat of the mold being conducted to the parison, such that upon introduction of fluid pressure into the parison the polymeric material deforms into the shape of the mold cavity. The mold is then cooled to cause the polymeric material to harden into the shape of the mold.

Typically, the mold is provided in a clam shell design wherein each half of the mold includes half of the interior cavity forming the balloon. The mold can therefore be wrapped around the parison and be easily removed to facilitate production. The parison itself can be heated by immersing the entire mold within a hot water, oil, glycerin, or other fluid bath and allowing the mold and parison to be heated via conduction. One problem associated with such a process is that heating of the parison is less than optimal. Heating via conduction, by its very nature, is a relatively slow process. Moreover, the substantial time it takes to heat the parison in the central section having the widest distance between the mold and the parison, in comparison to the narrow space at both ends, lends itself toward a substantial heat flow axially along the parison at these end sections, which itself tends to heat portions of the polymeric material at which balloon deformation is not desired. Accordingly, such systems typically need to employ some sort of cooling mechanism, such as a cold air jet, to keep the areas of the parison outside of the mold cool. One problem stemming from such a system is that temperature control or distribution across the entire polymeric tube is difficult. For bigger balloon sizes, in which the gap between the polymeric tube and mold wall is too large to give sufficiently fast transfer of heat, small amounts of water are often injected inside the mold between the parison and the mold for better heat conduction. However, it will be clear that this material is obstructing the free expansion of the parison inside the mold.

Moreover, with such conventional systems, it is not possible to heat different axial sections of the polymeric tube to different temperatures. For example, this may be advantageous when it is desired to create different physical properties within the balloon itself such as multiple areas of varying diameter, wall thickness, or multiple areas consisting of different materials to be heated to different temperatures. In a particular example one can think of the following: the tapering of the balloon from the central balloon section towards the shaft causes the wall thickness in the cone to increase towards the shaft section. This material distribution causes the folded balloon to be thicker in these cone sections than within the central section. For reasons of minimizing the profile of the product to achieve better access into the vascular system, one wishes to reduce the amount of material within the cone section and one way would be to heat the cone sections of the balloon to a higher temperature within the molding process in order to thin these sections. This effect of thinning would be the result of the combination of the applied axial force and the lower viscosity of the cone sections compared to the central cooler section. Although a section of the mold can be kept above the fluid bath, and thus have the effect of producing a cooler section in the mold, due to the slow heating process a sharp temperature transition is not possible. It is also not possible to set the metal mold to a different temperature than that to which the polymeric tube is heated. The mold must therefore be cooled down before the balloon can be removed.

In the construction of medical devices in addition to balloons, such as stents, guidewires, vena ceva filters and filter wires, the time required to cure adhesives and polymer coatings and thus facilitate manufacture, is relatively extensive. It would therefore be advantageous if a method could be devised for accelerating the curing process and thus manufacturing time for such medical devices.

Extrusion of polymers, such as used for medical products in the angiography field, has many inherent problems. One problem is the reduction of the transition zone occurring between two polymers being extruded on an intermittent basis, due to the combination of large volumes in the extruder head as compared to the volume of the medical device, such as a catheter tube, being extruded. There are also the high extrusion pressures present in combination with the elasticity of the polymers, as well as the shear forces occurring along the extruder wall.

Other extrusion-related problems include the fact that large, expensive, and complicated machines are necessary in the extrusion process to heat polymers homogeneously by a combination of mixing by the rotating screw, generating high shear forces, and simultaneous heat conduction through the heated inner surfaces of the extruder elements. Also, the processing time of polymers inside an extruder barrel and head is quite long. Such an extended processing time can have a signification degradation effect on the polymers being used, and in turn on the physical properties of the extruded product or so-called extrudate.

There are problems present in the cooling of extruded polymer products, including the length of cooling bath required, the need to have blowers to dry off the extrudate after being cooled in a cooling bath, and the need to quickly cool the heated polymers in the extrudate to minimize the effects of extended heating of the polymer material being extruded.

SUMMARY OF THE DISCLOSURE

In accordance with one aspect of the disclosure, a method of manufacturing medical devices is disclosed which includes directing microwave energy toward an exposed polymeric tube, forcing pressurized fluid through the tube to deform a section of the tube heated by the microwave energy, detecting movement of the deformed tube, and ceasing direction of the microwave energy and forcing of the pressurized fluid through the tube upon movement of the deformed tube being detected.

In accordance with another aspect of the disclosure, a medical device manufacturing system is disclosed which includes a microwave energy source adapted to impart microwave energy toward a workpiece, a fluid pressure source adapted to direct pressurized fluid through the workpiece, a sensor adapted to monitor a parameter associated with the workpiece, and a controller adapted to receive a signal from the sensor and direct signals to the microwave energy and fluid pressure sources.

In accordance with another aspect of the disclosure, a method of bonding medical device components together is disclosed which includes depositing adhesive between first and second components, engaging the first component against the second component with the adhesive therebetween, and subjecting the first and second components and adhesive to microwave energy.

In accordance with another aspect of the disclosure, a microwave field is utilized as the heat source for the heating and mixing of the polymers at a point just before they are forced through an extruding tip and die orifice. Solid disks of various polymer materials are stacked and pushed towards an open tip and die combination within an extruder, whereupon the microwave field acting as a heat source is applied just before the tip and die exit.

In accordance with another aspect of the invention, new polymer disks of varying properties are added in a continuous fashion without interrupting the forces pushing on the disk stack to achieve a continuous feeding process for the microwave extruder apparatus. An appropriate gripping and forcing mechanism acting on the sides of the stacked disks, or on the end of the stacked disks, causes them to move forward towards the microwave heat source and extruder tip and die combination.

In accordance with another aspect of the invention, the microwave energy is applied to the polymer disks by generating a microwave beam that penetrates through the extruder tip and die material, and that microwave beam can be focused through use of appropriate lenses and mirrors. The extruder tip and die can be formed of a microwave-transparent material such as Quartz.

In accordance with another aspect of the invention, the temperature of the polymers being melted in the extruder tip and die are optically sensed, and that is utilized in a feedback loop to the microwave heat source to enable precise control of the temperature of the polymer.

In accordance with another aspect of the invention, individual polymer disks are initially prepared by utilizing polymer pellets that are subjected to homogeneous heating using variable frequency microwaves, also known as electronic mode stirring.

In accordance with another aspect of the invention, the final hub ring for a catheter product is formed during the process of forming the catheter tubing, through the use of a split-mold molding process.

Finally, in accordance with another aspect of the invention, a silver cooling pipe carrying a cooling medium is disclosed as one method of cooling the extruded catheter tubing product being formed by the microwave-heated extrusion die process. A cooling bath can additionally be used to cool the extrudate so formed.

These and other aspects and features of the disclosure will become more apparent upon reading the following detailed description when taken in conjunction with the accompanying drawings.

BRIEF DESCRIPTION OF THE DRAWINGS

FIG. 4 is a diagrammatic representation of another alternative embodiment of a molding apparatus constructed in accordance with the teachings of the disclosure;

FIG. 5 is a diagrammatic representation of another embodiment of a molding apparatus constructed in accordance with the teachings of the disclosure.

Figure 1:
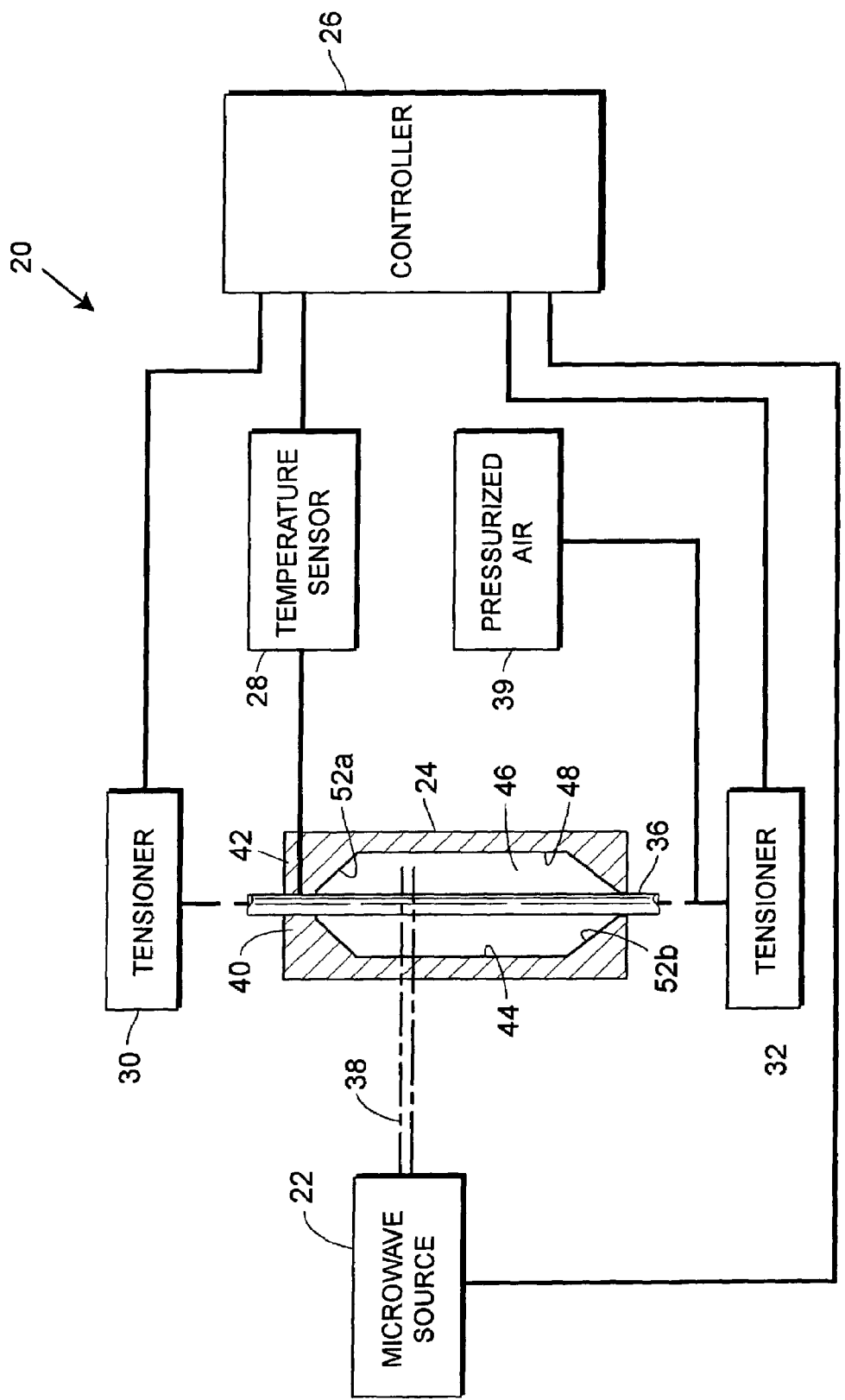
FIG. 1 is a block diagram of a balloon catheter molding apparatus constructed in accordance with the teachings of the disclosure.

While the disclosure is susceptible to various modifications and alternative constructions, certain illustrative embodiments thereof have been shown in the drawings and will be described below in detail. It should be understood, however, that there is no intention to limit the disclosure to the specific examples disclosed, but on the contrary, the intention is to cover all modifications, alternative constructions, and equivalents falling within the spirit and scope of the invention as defined by the appended claims.

DETAILED DESCRIPTION OF THE DISCLOSURE

Referring now to the drawings, wherein like reference numerals indicate corresponding elements, and with specific reference to FIG. 1, a balloon catheter molding apparatus, constructed in accordance with the teachings of the disclosure, is generally referred to by reference numeral 20. As described herein, the apparatus 20 may be advantageously employed for the manufacture of balloon catheters and angioplasty balloons, but can be employed in conjunction with many other types of polymeric devices including, but not limited to, other medical devices or components of medical devices, such as contact lenses, graft material, hub mainfolds and the like.

Figure 3:
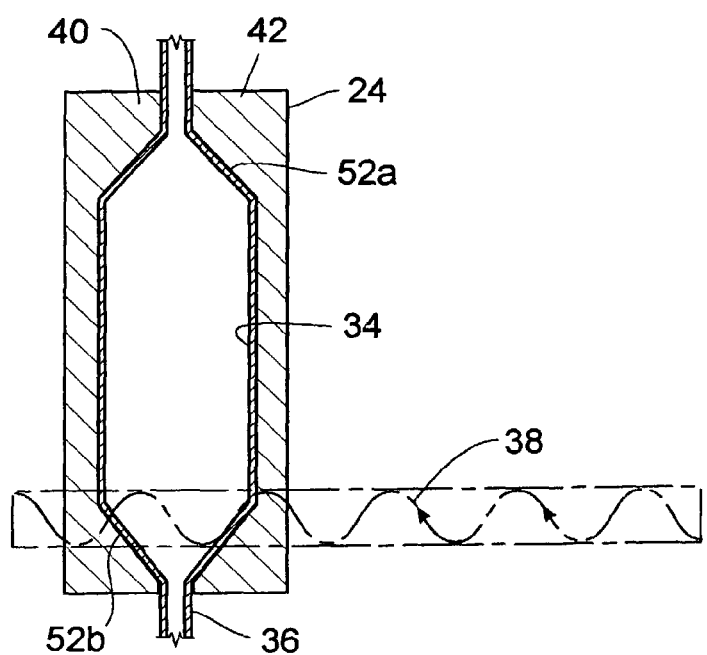
FIG. 3 is a schematic representation of one embodiment of a molding apparatus constructed in accordance with the teachings of the disclosure.

Referring again to FIG. 1, the system 20 may include a source of microwave energy 22, a mold 24, a controller or processor 26, a temperature sensor 28 and first and second tensioners 30, 32. Employing such elements, the apparatus 20 can form a balloon 34 (see FIG. 3) from a workpiece or parison 36. More specifically, the parison 36, which may be provided in the form of a tube or cylinder of polymeric material, is provided within the mold 24. The source of microwave energy 22 then directs a beam or band 38 of microwave energy toward the mold 24, with the microwave energy heating the polymeric material. Prior to heating, during heating, or once heated, pressurized fluid, which may be provided in the form of compressed air from a compressor 39, is injected through the workpiece 36 causing a portion of the workpiece 36 within the mold 24 and heated by the microwave source 22, to expand within the mold 24 as shown best in FIG. 3.

Figure 2:
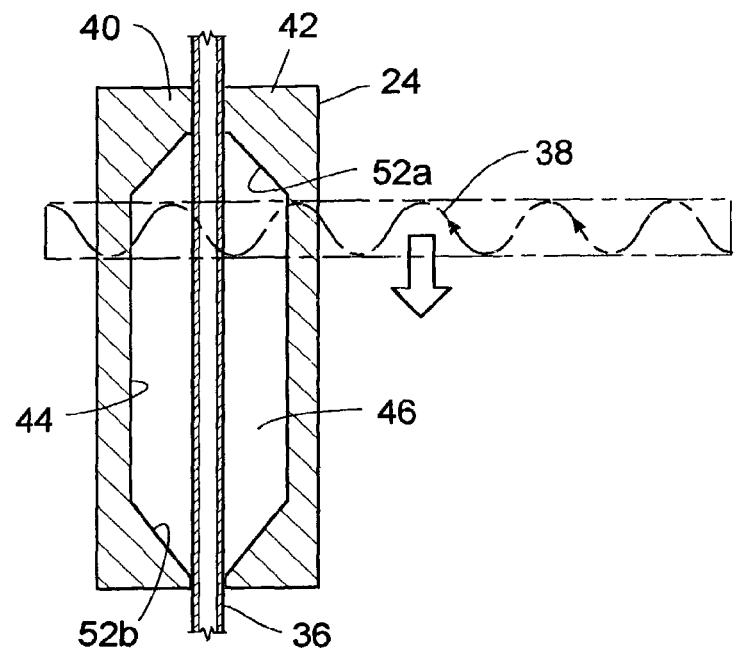
FIG. 2 is a diagrammatic cross-sectional view of a mold and molding process constructed in accordance with the teachings of the disclosure.

Referring now to FIG. 2, the mold 24 is shown in further detail. While it is to be understood that the mold 24 may be provided in a variety of forms, one workable embodiment provides the mold 24 in the form of a clam shell mold having first and second complementary halves 40, 42 with each half 40, 42 having a recess 44 which, when combined, forms the entire mold cavity 46. The cavity 46 is shaped to the desired profile 48 of the balloon 34. In the depicted embodiment, each recess 44 includes a cylindrical outer surface 48 as well as top and bottom canted or conical surfaces 52a, 52b.

Preferably, the mold 24 is manufactured from a microwave-transparent material having a low dielectric loss characteristic, such as a ceramic material or quartz material, although many other types of non-metallic materials, including but not limited to Teflon®, or boron nitride, can be employed with similar efficacy. If the mold 24 is made of Teflon®, for example, or another microwave transparent material that is a poor thermal conductor, application of the microwave beam will allow the temperature of the balloon to be raised to the heatset temperature by applying further microwave energy after the balloon has been blown.

Figure 6:
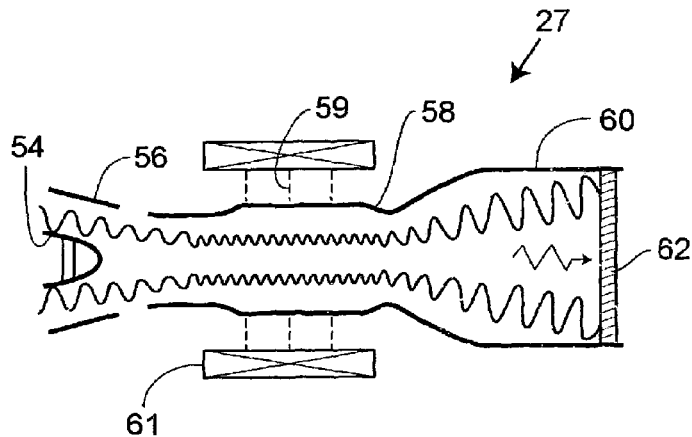
FIG. 6 is a schematic representation of a gyrotron.

With regard to the microwave source 22, it may be provided in the form of a magnetron adapted to emit microwave energy at a frequency within the range of 900 MHz to 30 GHz, or a Gyrotron adapted to emit microwave energy at a frequency within the range of 20 GHz to 140 GHz, and a corresponding wavelength within the range of 332 mm (900 MHz) to 2.14 mm (140 GHz). A common frequency for magnetrons is 915 MHz, 2450 MHz, 5800 MHz, and 24,125 MHz. A common frequency for Gyrotrons is within the range of 20 to 140 GHz. While these are commonly used frequency ranges for magnetrons and gyrotrons, respectively, it will be understood that even microwave frequencies falling outside of these ranges can be used and suitably so with the present invention. As shown in FIG. 6, the Gyrotron may consist of an electron gun having a cathode 54, an anode 56, a resonance chamber 58 immersed in a strong magnetic field 59, and a collector 60. The magnetic field 59 may be generated by superconducting magnets or solenoids 61. When the cathode 54 is energized, accelerating electrons emitted thereby enter the magnetic field 59 and start to spiral, or gyrate, at a high relativistic speed and in very small loops. An advantage of using microwave energy as opposed to, for example, infrared, is the tremendous speed of heating.

For example, using a magnetron injection-type electron gun with the cathode 54 potential at ten kilovolts and a magnetic field 59 of twelve Tesla will result in the electrons being gyrated in a spiral with a radius of 30 micrometers and a cyclotron frequency of 330 GHz. Changing the magnetic field 59 enables the frequency to be changed accordingly. In order to obtain a high frequency wave, the resonant cavity should be designed in such a way that its geometric size matches a harmonic of the wavelengths created by the gyrating electrons. The electromagnetics transmitted through the radio frequency (RF) window 62, and by means of a waveguide 63, can be transported to the target. Manufacturers of gyrotron systems deliver such gyrotrons with built-in mode converters to convert the beam to a gaussian-shaped He11 mode, which can be guided through a circular wave guide with low loss. For example, Insight Product Company of Brighton, Mass. provides such a system. The He11 mode radiated from an open-ended circular waveguide has an axisymmetric narrow Gaussian beam with well-defined polarization and direction, and low-side lobe level enabling the use of simple optical components like metal mirrors and HDPe lenses to focus the beam on a target.

With regard to the power level required to heat the workpiece 36, if the panson is manufactured of Pebax®, in order to bring the workpiece 36 from room temperature to 140° Celsius, and be able to blow a balloon, the required energy can be calculated according to the following. By way of example only, a typical parison tube can be, for example, 1 mm in an outer diameter, and 0.6 mm in the inner diameter, and have a length of 32 mm. The volume of such a tube therefore is 12.8 cubic mm. Taking a CP value of 1500 Joules per kilogram degree Celsius and a density of 1.1 grams/cm$^3$, this means that 2.54 Joules are required to heat the parison from room temperature to 140° Celsius. A commercial low power gyrotron, for example, that manufactured by Insight Product Co., which offers a 24 GHz continuous wave gyrotron with the output power being continuously regulated in the range of 0.1–3 kW by varying the electron beam voltage, up to a maximum of 12 kV, can be defocused roughly to its wavelength, i.e., 12 mm. Therefore when the parison is placed in the focus of the beam about $\frac{1}{12}$ of the beam will hit the target. Assuming a 50% absorption of the energy, this means that at 0.1 kW CW output power, it will take about 2.54 Joules/(100 (Joules))/24)=0.6 seconds to heat the parison.

Referring again to FIG. 1, not only can the apparatus 20 be used to manufacture balloons using microwave energy, but through the use of the temperature sensor 28 and the processor 26, a feedback loop is provided to thus enable the gyrotron 22 to be modulated based on the heated temperature of the workpiece 36. A suitable temperature sensor would be a model number OS 1592 Fast Response Infrared Fiber Optic Thermometer available through Newport Corporation, which gives about forty readings per second, or an infrared temperature sensor from Heitronics Corporation.

To control the power output of the gyrotron the pulse links of the input voltage on the cathode 54 could be adjusted. By doing so, it would be possible to, for example, operate a 10 kilowatt gyrotron at an average power level of 5 watts or even lower. If the end temperature should be controlled within plus or minus 2° C. (3.6° F.), the rise of the temperature should be less than 2° C. (3.6° F.) for every pulse in between the sensor readings. Therefore, there should be at least 60 readings in between 20° and 140° Celsius assuming a constant absorption coefficient of the polymer material as a function of the temperature. The update frequency of the Heitronics IR sensor is 200 Hz. Taking the earlier calculated 0.6 seconds to rise the parison 1200 Celsius into account, which is 200° Celsius per second, and assuming for the time being a simplistic model of a linear rise, reading the IR sensor at 200 Hz will result in an accuracy of 1° Celsius. This demonstrates that it is not unrealistic with existing equipment and sensors to realize a control temperature rise in the parison to 140° Celsius with a precision of ±2° C. within less than 2 seconds.

In an alternative embodiment, the gyrotron beam could be defocused so that only a small percentage of the beam impinges upon the sample. For example, this could be done using a cylindrical lens. In so doing, a much smaller temperature rise could be achieved and the gyrotron could be stopped once the required temperature is reached. Similarly, the current of the cathode could be reduced thereby reducing the output power of the gyrotron. In a still further embodiment, use of a power splitter such as a polarizing splitter could be used to enable a 50/50 power split. Three of these such splitters in series would enable the power level to be reduced to 12.5%. One could also use the 50/50 splitting operation to do multiple balloon blowing at the same time. Defocusing the laser beam would also allow to heat multiple parisons at the same time. Excess energy could be redirected and absorbed by a water load.

In order to focus the microwave output upon the workpiece 36 and provide an even heating profile across the balloon 34, the embodiments depicted in FIGS. 4 and 5 may be employed. In both embodiments, lenses are employed to focus the beam. For example, as shown in FIG. 4, the microwave source, which may be provided in the form of a gyrotron 22, directs microwave radiation through a waveguide 63 to a first lens 64, which in turn directs the focused microwave beam to a second lens 66. The first lens may be provided as an HDPE lens, while the second lens 66 may be an accurate or focusing metallic mirror. Such lenses are readily, commercially available, such as through Farran Technology. One way of fabricating the balloon is to put the output of the circular wave guide 62 in the focal point of the HDPE lens in order to create a parallel beam and to direct that beam into a focusing mirror as shown in FIG. 4. Such operation will give a slightly inhomogeneous power distribution over the length of the polymer tube.

Alternatively, the beam could be scanned along a part of the tube to achieve a more uniform temperature distribution. This can be done by focusing the beam on a mirror which makes an angle, e.g., 45°, with the optical axis and which rotates around that optical axis as shown in FIG. 5. The beam is thereby scanned in a plane perpendicular with the optical axis. By putting the scanning mirror in the focal point of the parabolic mirror, a system is created wherein the beam can be scanned in one direction along the parison. This also allows a convenient way in which to integrate the infrared sensor. The microwave is focused by the scanning mirror and the focusing lens on a small part of the parison, e.g., on the order or the wavelength. The IR detector's position is perpendicular and is focused to the starting point of the scanned length on the parison.

As shown in FIG. 5 therein, a second lens 66 is a rotating lens which thus enables the focal point of the microwave energy to be not only focused, but moved across the axial length of the balloon 34. Moreover, the first lens 64 is provided in the form of a parabolic lens or mirror. The microwave beam is focused by the scanning mirror and the focusing lens on the small part of the parison. The infrared detector is positioned in a perpendicular direction and is focused to the starting point of the scan length on the parison. While the beam scans across the parison, the infrared sensor monitors the parison. As every point along the parison is receiving the same energy, all points will go to the same heated temperature. Once heated to the correct temperature, the parison is drawn quickly into the mold and the balloon can be blown. In another embodiment one could close a clamshell mold once the parison has reached its temperature. This would avoid having to move the parison. In the case of a pulse microwave system, a much higher pulse frequency is chosen achieving a significant overlap between two adjacent spots. In the case of a CW gyrotron even distribution is automatically obtained. It should be understood that there will be a drop in temperature while the parison is being transported into the mold, or during the closing of the mold, after the heating operation. This can be compensated for by monitoring the rate of this drop and, as the time of transportation is known, compensate for the drop in the heating cycle. This also allows a temperature profile to be achieved along the parison. For example, if it is desired to heat a certain section of the parison to a higher temperature, the infrared sensor can be focused at the high temperature and once the lowest temperature of the profile is reached, those pulses passing over the low temperature sections can be stopped.

Figure 7:
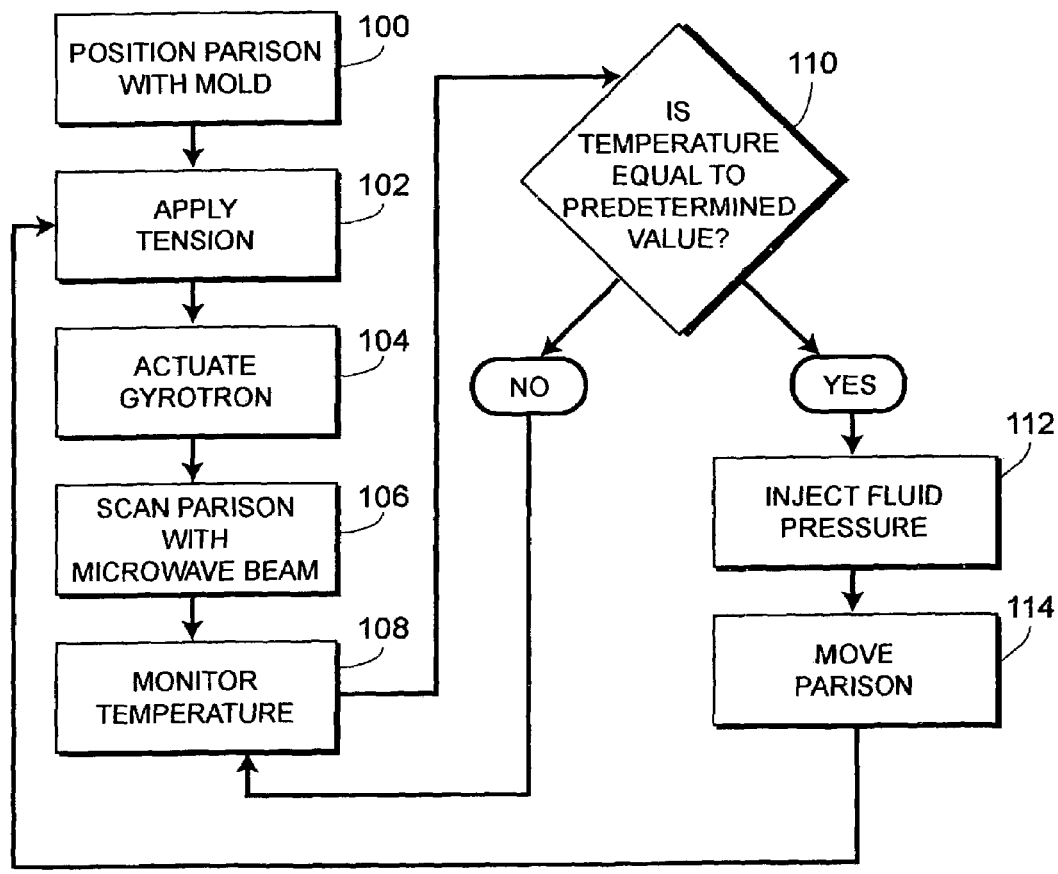
FIG. 7 is a flowchart depicting a sample sequence of steps which may be taken accordingly to the method disclosed herein.

Turning now to FIG. 7, a flowchart depicting a sample sequence of steps which may be taken according to the method of the disclosure is provided. As shown therein, a first step would be to position the parison workpiece 36 within the mold, as indicated by a step 100. Thereafter, if desired, the tensioners 30 and 32 may be actuated if desired to place the parison under tension during the heating process aided by step 102. The tensioners 30, 32 may be provided in a variety of readily available forms including, but not limited to, hydraulic or pneumatic clamps, rotating mandrels or spools, or the like. Once under tension, the gyrotron can be actuated, as indicated in step 104, with the microwave beam generated thereon being scanned across the parison as indicated by step 106. During such scanning, the temperature of the parison is continually monitored by the temperature sensor 28 as indicated in step 108. If the monitored temperature is equal to a predetermined level or within a predetermined range as is determined by the controller 26, as indicated in step 110, the compressor 39 can be actuated to direct pressurized air through the parison as indicated in step 112. Alternatively, the controller 26 may employ an algorithm wherein the gyrotron 22 is modulated in intensity based on the temperature readings. Thereafter, the parison can be moved through the mold 24 as indicated in step 114 and positioned to restart the process. Alternatively, if the monitored temperature is not within such a predetermined range, the temperature continues to be monitored until reaching such level.

Figure 8:
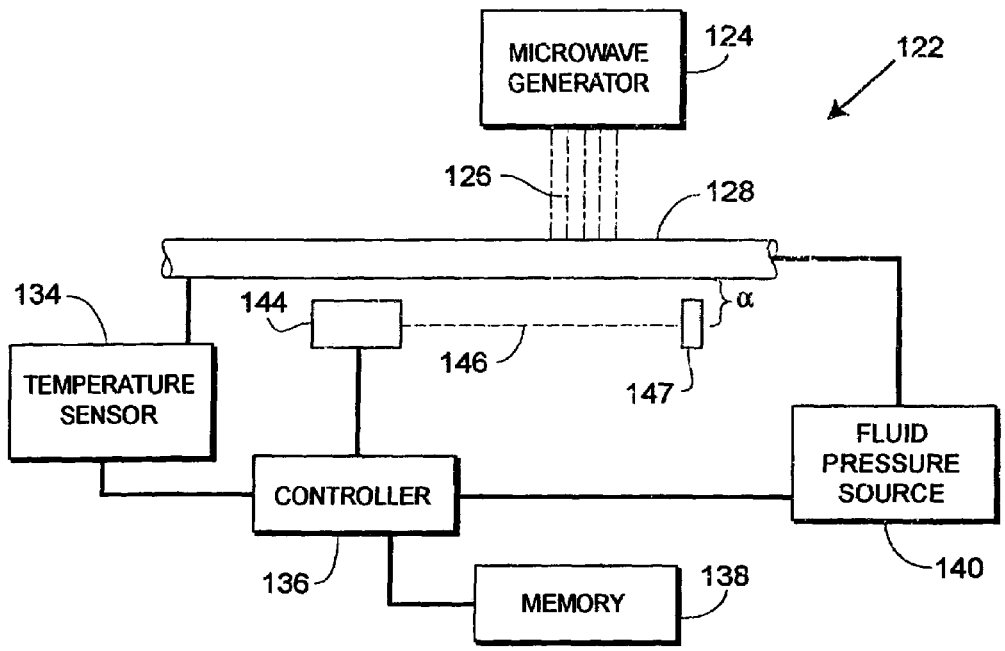
FIG. 8 is a schematic representation of a medical device manufacturing system constructed in accordance with the teachings of the disclosure, with the medical device being heated.
Figure 9:
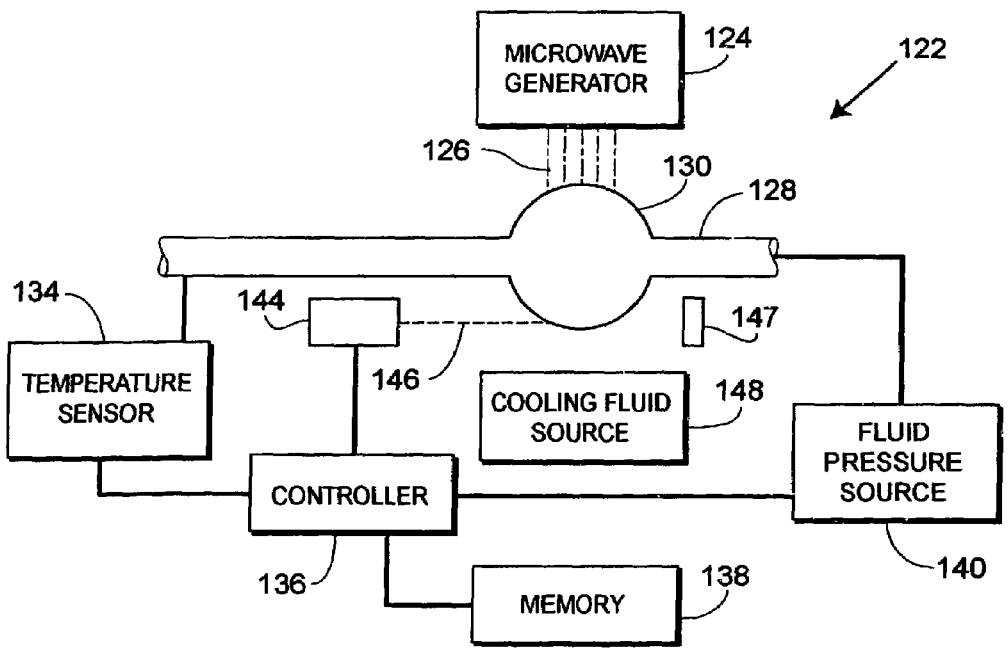
FIG. 9 is a schematic representation similar to FIG. 8, but with the medical device being pressurized and expanded.

In a still further embodiment illustrated in FIGS. 8 and 9, a medical device could be constructed without using a mold of any kind. In such a system, referred to herein as free blowing, manufacturing could be facilitated and accelerated in that the additional labor required for adding and removing the mold or removing the workpiece from the mold can be eliminated. More specifically, as depicted in the figures, a system 122 could be provided similar to the above-referenced embodiments in many ways but not including the mold. A gyrotron 124 or other source or microwave energy is provided to direct a beam of energy 126 toward a workpiece or parison 128 as indicated above. The beam 126 can be scanned back and forth over the entire parison 128, or directed to a specific location such as the desired location for a balloon 130 (FIG. 9) forming part of a balloon catheter, or the like.

An added benefit of manufacturing a medical device 20 without a mold is the free access to the parison 128 it affords, thereby facilitating rapid and complete temperature detection. As indicated in the figures, a temperature sensor 134, (or temperature sensors) could be provided so as to take accurate and frequent temperature sensor readings and in turn direct a temperature signal to a controller 136. The controller 136, which could be any form of microprocessor based computing device, or even just an analogue electronic system, can compare the read temperature of the parison 128 and, upon reaching a threshold temperature stored in a memory 138, dispatch a signal to a fluid pressure source 140 to direct a stream of pressurized fluid into the parison 128 as indicated in FIG. 9.

Since the gyrotron is an electron beam, the energy of the gyrotron beam 126 can be modulated exactly and quickly. In other words, while sweeping the beam 126 over the parison 128, the start and stop positions for the beam, as well as the energy distribution along the swept path, can be precisely controlled. This can be at a single energy level to heat the parison 128 to the same temperature between start and stop positions, or a temperature distribution along the parison can be generated by modulating the energy while sweeping. Since the temperature absorption rate of the workpiece is a non-linear function of the temperature of the workpiece, in order to be able to bring the workpiece to any predefined temperature, a feedback loop provided by the temperature sensor 134 and the controller 136 is advantageous. For example, an infrared radiation pyrometer such as model number KT22 manufactured by Heitronics Corporation is useful in that it has a response time of less than five milliseconds to an accuracy of 0.1° Kelvin. The temperature sensor manufactured by Impac under its model number Infratherm YP10 is also useable in that it has a response time of two milliseconds. Moreover, both sensors can focus down to spot sizes smaller than 0.5 millimeter, which is smaller then the diameter of most parisons.

Using such a feedback loop, while sweeping the product multiple times with an electron beam, one can monitor the temperature of the product at a single point and stop the heating process when the predefined temperature has been achieved. In such a way, any temperature within the range of, for example, room temperature to 400° C., can be achieved within less than a second. Using the KT22 pyrometer sensor it is possible to measure only at a single point, but there are also infrared line scanners, which can sense the temperature along the complete product. If the entire tube is scanned with the microwave beam using the same energy level, then sensing a temperature at a single point along the tube will be sufficient to obtain a good measure of temperature along the entire product. Even when a temperature profile is created along the tube by changing the energy of the microwave beam as a function of the position along the tube, measuring the temperature at a single point which receives the highest energy is sufficient to tell the temperature along the entire line.

Referring now specifically to FIG. 9, it can be seen that upon introduction of fluid pressure into the workpiece 128 by the fluid pressure source 140, the heated section (balloon 130) of the parison 128 is expanded. This is because the heat generated by the gyrotron is sufficient to heat and weaken the parison 128 at the desired location for the balloon to a greater degree than the remainder of the parison 128. Accordingly, the force generated by the fluid pressure is able to deform the heated, weakened section of the parison 128, while leaving the remainder unchanged.

In order to accurately form the balloon 130, without the use of a mold, at least one position sensor 144 can be provided. For example, as indicated in FIG. 9, an optical scanner such as a laser scanner can be positioned so as to direct a laser beam 146 across to a receiver 147 at a distance a from the parison 128 corresponding to the desired dimension for the balloon 130. Upon the balloon 130 reaching such dimension, the beam 146 is broken whereupon the position sensor 144 then directs a signal to the controller 136 indicating same. Upon receipt of such a signal, the controller 136 then directs the fluid pressure source 140, or a valve associated therewith, to reduce the pressure of the fluid inside the parison 128 and stop further expansion. Another embodiment would use a focused microwave to heat a small portion of the parison and upon expansion of that section, signaled to the processor by the signal of the distance sensor, the processor would force to either move the parison in axial direction or move the microwave beam. In other words, the balloon blowing process would be a continuous process along the axial direction instead of a simultaneous process.

By repeating these processing steps over the same balloon section, one could expand the balloon in gradual steps.

Moreover, a cooling source 148 can be provided to facilitate curing of the parison 128 upon the balloon reaching its desired dimension. For example, low temperature nitrogen gas, air, helium gas, or the like can be blown against the balloon 130 when cooling is desired. Such cooling gas, in conjunction with the cessation of microwave energy and fluid pressure, will facilitate immediate setting of the polymer material. In addition to Pebax® and the other materials indicated above, the system 122 can be used in conjunction with various other types of materials, including, but not limited to, polyimide, polyimide 12 PEEK (polyetheretherketone), PTFE (polytetrafluoroethylene) and PET (polyethylenterephthalate), polyetherpoly(2,6-dimethlyl-phenylene-ether), polyetherketone, blends of such materials, or any other high or low temperature polymer.

The parison 128 can also be extruded or otherwise manufactured from two or more polymers with an objective to create balloons with a greater variety of mechanical performance in different sections of the balloon. A typical example would be to create a balloon with a non-compliant central section and a compliant end section in order to produce a 'dog-bone' type of balloon, enabling the injection of a drug in the enclosed space between the central section of the balloon and the arterial vessel wall. The compliant end sections would allow for a seal with the vessel wall, whereas the non-compliant central section would allow for annular space between the balloon and the vessel wall. If the second polymer has a different glass transition temperature than the first polymer, as well as a different mechanical strength, both polymers have to be heated to different temperatures, in order for both polymers to be amenable to balloon formation upon injection of fluid pressure. In other words, using the ability of the microwave heating process to heat different sections of the parison to different temperatures, one is enabling such balloon designs combining two or more polymers. Although, not limited to such a temperature it has been found by the inventor that some high strength polymers such as polyimide with a glass transition point of at least 215° C. are advantageous in the creation of high strength thin walled balloons The required high balloon blow-molding temperatures make it impossible to process these materials using the conventional balloon blow process due to the axial flow of energy. The speed of microwave heating offers the ability to free-blow balloons with a temperature gradient along the parison of at least 25° C. per millimeter inside the mold. As this cannot be done by other means due to the axial flow of energy, it offers more materials to be used along the axial line of the parison. As explained before, the speed of heating also enables a balloon to be blown in less than two seconds at temperatures higher than 140° C. offering the advantage of reduced thermal degradation of the polymer during the balloon blow process.

Figure 10:
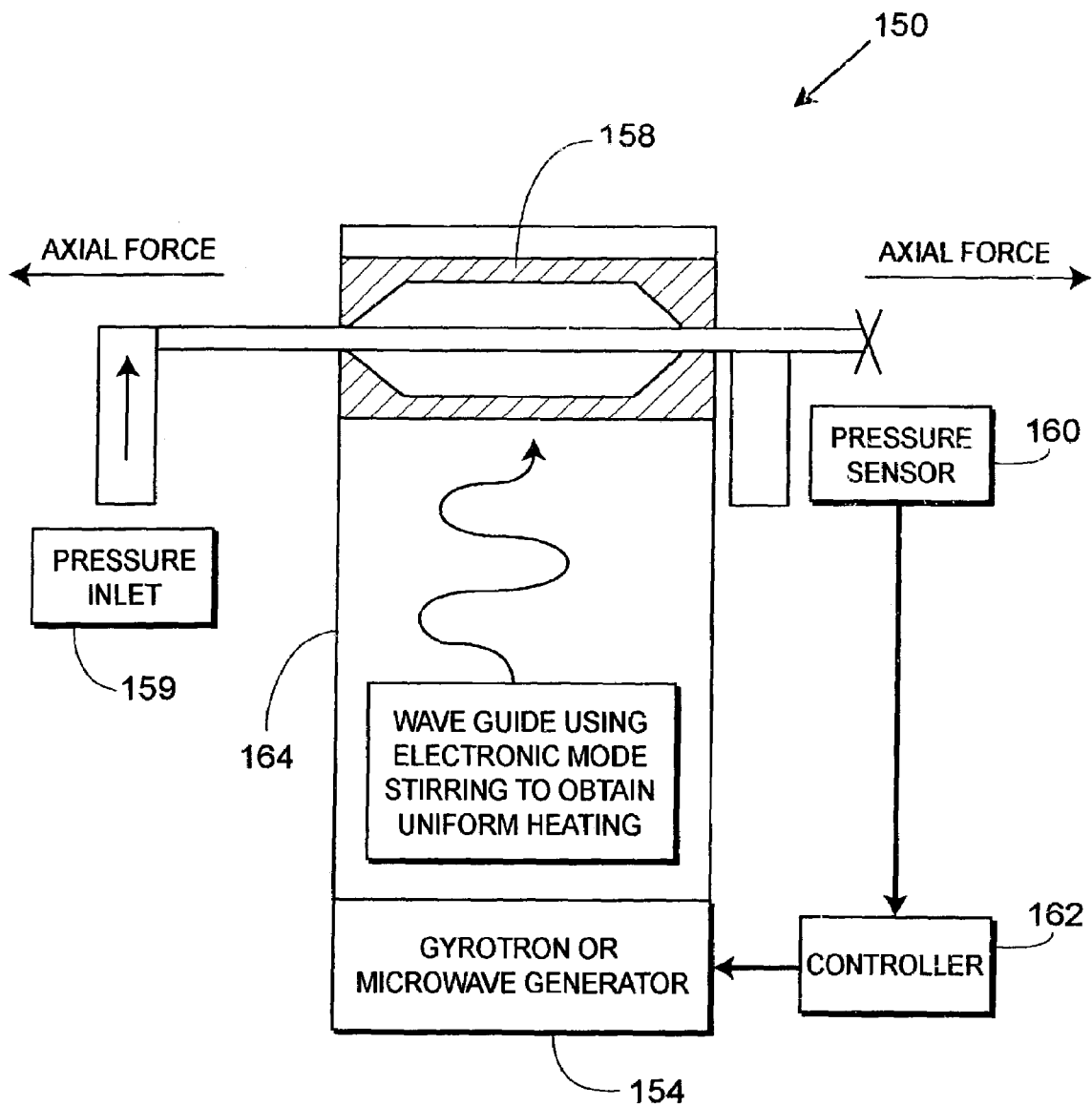
FIG. 10 is a schematic representation of a medical device manufacturing system employing a pressure sensor.

In a still further system 150 depicted in FIG. 10, fluid pressure is directed through a parison 152 prior to and/or during heating of the parison 152 by gyrotron 154. Accordingly, once the parison 152 reaches a threshold temperature at which the material of the parison becomes too weak to sustain its shape, it will expand, forming a balloon. Such an embodiment could be used with or without a mold 158, with fluid pressure being directed through the parison 152 via a fluid pressure source 159.

In such an embodiment, the drop in fluid pressure within the parison 152, resulting from the expansion of the parison 152, can be used as an indirect temperature control to deactivate the gyrotron 154, and thus cease heating of the parison 152. More specifically, as indicated in FIG. 10, a pressure sensor 160 could be provided to constantly monitor the fluid pressure within the parison 152. The pressure sensor 160 in turn sends a corresponding signal to a controller 162. Once the parison 152 reaches a temperature at which the fluid pressure is sufficient to deform the parison 152 and form the balloon, the pressure within the parison 152 will drop due to the expansion of volume. The resulting drop in pressure will be transmitted via a corresponding signal from the pressure sensor 160 to the controller 162, with the controller 162 in turn directing a signal for deactivating the gyrotron or other microwave source 154. As the heating is done very quickly, very responsive pressure sensors are desirable, such as a Kistler model No. 601A or 701A.

As indicated above, microwave energy can be generated by a gyrotron used in conjunction with a plurality of fixed and/or moveable lenses to create a quasioptical system. However, in an alternative embodiment, one could also place the workpiece within a waveguide. However, since only certain wave modes fit within a certain guide geometry, only certain wave modes are directed to the workpiece giving in essence a very non-uniform heating. Therefore, in order to achieve uniform heating, one could apply either mechanical or electrical mode stirring. In mechanical mode stirring, such as used in a variety of conventional microwave heaters, one changes continuously the geometry of the waveguide in order to change the preferred wave mode. In electronical mode stirring (variable frequency) one sweeps repeatedly and continuously through a frequency band or domain causing the same mode-stirring effect. To achieve a very uniform heating result within this almost instantaneously heating process, it is clear that the mode-stirring frequency has to be very high and the stirring has to run through a large spectrum of wavemodes and by that one could say that an electronic mode-stirring is by definition more applicable.

In the embodiments specifically mentioned above, a balloon catheter is being manufactured. However, it is to be understood that microwave heating can be used in manufacturing various other medical, including angiography, devices or components including, but not limited to, connecting a manifold to a catheter shaft using adhesive, connecting layers of a medical device together using a microwave absorbent material such as a carbon in between the layers or curing a polymer coating or the like to the outer surface of a stent, filter wire, or other polymer metal or ceramic device. Under conventional systems, the adhesive is simply allowed to cure under room temperature, often resulting in relatively long manufacturing cycles, or displacement of the adhesive turning the process. However, by directing microwave energy toward such adhesives, curing time are greatly reduced. The process can be further accelerated by including electrically conductive fibers in the adhesives. A very suitable electric conductor is carbon, which comes in a variety of shapes and powder sizes, on the order of microns and nano-sized fibers.

In order to enable such microwave energy to be used in curing a polymer coating onto a metal substructure, a variable frequency microwave applicator can be employed. Microwaves are often not used in conjunction with metal objects in that sparking or arcing results from excessive charge buildup in the metallic material in the presence of standing wave patterns. However, with a variable frequency microwave technique, the electric fields generated are electronically stirred and the microwave energy is not focused on any given location for more the a fraction of a second.

The dynamics of charge buildup that lead to sparking are therefore never achieved, hence leading to no arcing. As such, this enables the positioning of stents, filter wires, vena ceva filters, or any other metal structure inside a variable frequency microwave applicator.

Figure 11:
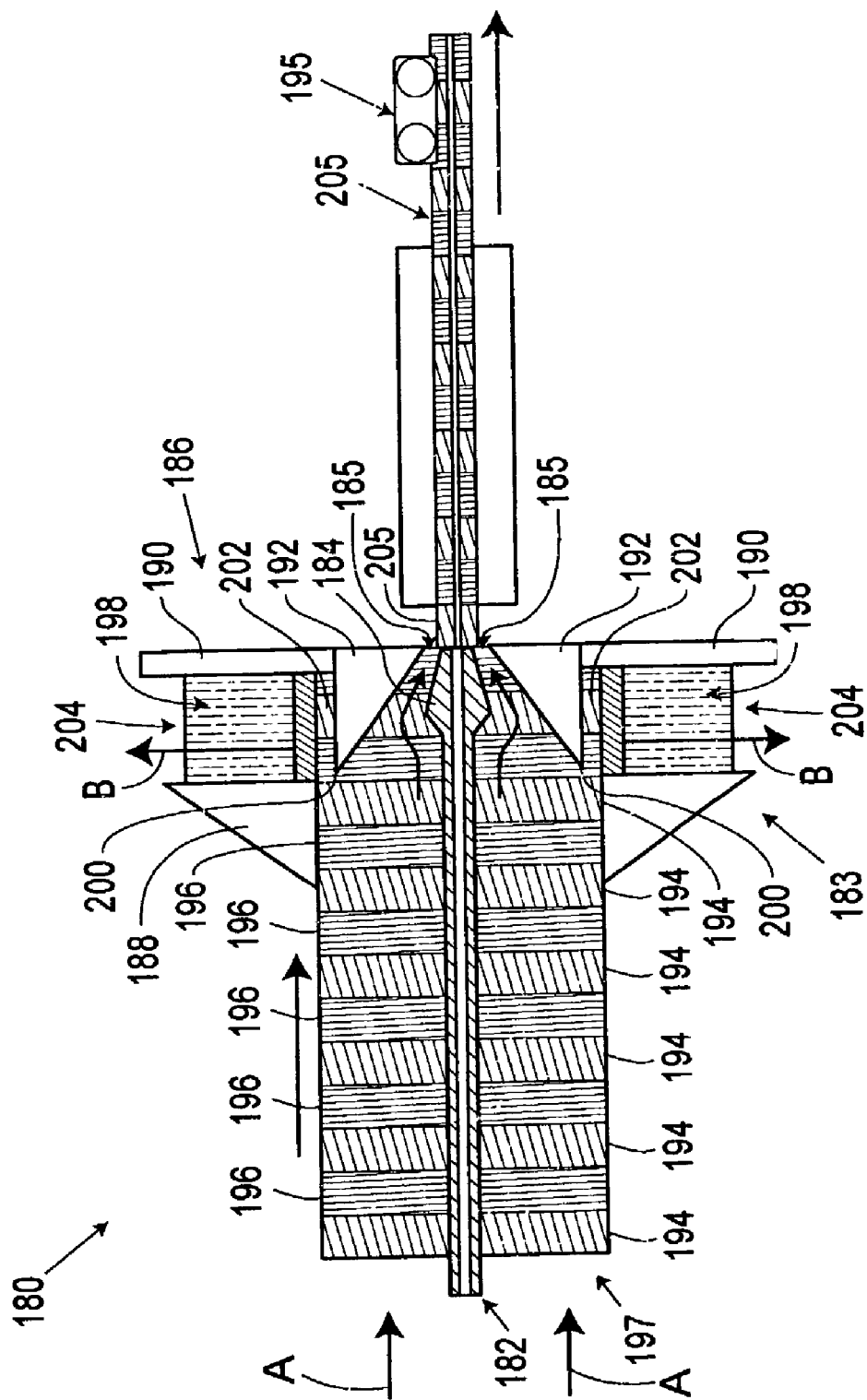
FIG. 11 is a cross-sectional view of the microwave-heated extrusion die apparatus in accordance with the teachings of the disclosure.

There is shown in FIG. 11 one embodiment constructed in accordance with the disclosure of a microwave polymer extruder apparatus, generally denoted by reference numeral 180. Extruder apparatus 180 comprises a rod support or air tube member 182, and an extruder tip and die combination 183, which includes an open die tip 184, and a die, generally denoted by reference numeral 186. Die 186 comprises initial die block members 188, a die support wall 190, and cutter die members 192. The various die members 184, 186, 188, 190, and 192 are preferably formed of a suitable non-metallic, microwave-transparent material, so as to allow the microwave energy to reach and heat the polymer material on the inside of the extruder apparatus. Such suitable materials include—just like the microwave transparent materials as discussed above relative to balloon mold 24—ceramic material, quartz material, glass material, and other non-metallic materials, including but not limited to Teflon® and boron nitride. It will be understood that, if desired, the die tip 184 can be deleted in certain applications, whereupon the die 186 acts as a hollow structure with an inlet opening (per die block member 188) and an outlet opening (per die exit opening 185).

A series of solid polymer feedstock members, namely solid polymer disks 194 formed of a first polymer material, and solid polymer disks 196 formed of a different, second polymer material, for example, are stacked one against the other to form a pressed stack 197 of polymer feedstock material for the combination tip and die 183. The respective polymer materials making up respecting polymer disks 194, 196 have differing properties selected to form the desired extrudate 205. Suitable polymer materials for use with extruder apparatus 180 include Pebax®, as well as the other moldable and extrudable materials as already discussed and listed above relative to cooling source 148. In any event, stack 197 is supported by air tube 182 and is pushed therealong by a suitable forcing mechanism (described later herein), in the direction of arrows A in FIG. 11, towards the extruder die 180. The air tube 182 receives a supply of air forced through it, to assist in the formation of the tubular extrudate 205. A caterpillar drive 195, see FIG. 11, operates as a means for removing the extrudate 205 from the extruder apparatus 180.

Figure 12:
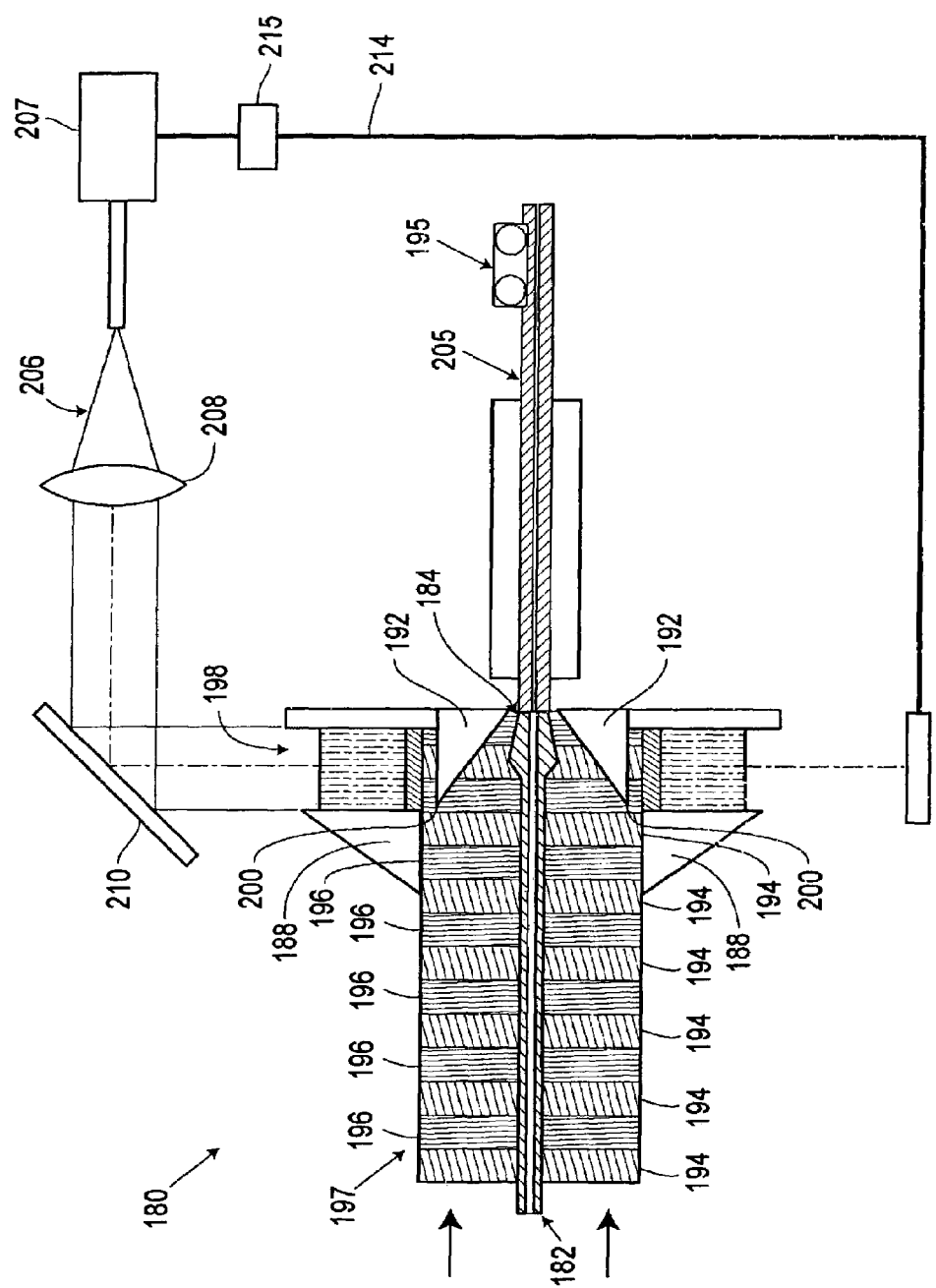
FIG. 12 is another side cross-sectional view, similar to FIG. 11, and also schematically showing the microwave energy source and related control system components.

As seen in FIG. 12, a microwave energy field, generally denoted by reference numeral 198, is applied against the polymer disk stack 197, but only in that region between the area just before the outer tips 200 of cutter die members 192 and the die exit opening 185. Importantly, as the various die members are microwave-transparent, they are not affected by the microwave energy field 198, and in turn, the microwave energy field 198 is not hampered, deflected or otherwise changed by the various die members.

Referring to FIG. 11, the outer edge material 202 of the polymer disks 194, 196 which are being pushed towards the die tip 184 are cut off by the sharp outer tip edge 200. This cut-off residue polymer material 202 leaves the die and tip combination 183 through the residue openings 204, in the direction of arrows B. In this fashion, the remaining polymer disks 194, 196 are melted (by the microwave energy field 198) only just before engaging the cutting edge 200 on the proximal side (left side in FIG. 1) of the tip and die combination 183. The pressure of the advancing solid disk stack 197 forces the molten polymer through the tip and die combination 183. The melted disks 194, 196 will form a stream of pressurized molten polymer in the tip and die combination 183 moving towards the tip 184 and outlet opening 185, and because of the low shear forces they will only mix at their interfaces. It will be noted that the conically-shaped and hollow die tip 184 is connected rigidly to the end of the air tube 182, so that the air tube feeds air directly to the very end, i.e. distal end, of the die tip 184. The conical shape of the distal end of the die tip 184, combined with the conical shape of the die 192, causes a narrowing split (see curved arrows in FIGS. 11 and 12), about die tip 184 in the direction of the die outlet opening 185. Thus, the molten polymer flows around the proximal (left end in FIG. 11) end of die tip 184 and out through the die outlet opening 185. The purpose behind having the outer dimension of the cutting edge 200 be smaller than the outer dimension of the polymer disks 194, 196, is to make sure that there is no backflow of molten polymer material obstructing the extruding operation occurring at the tip and die opening 185. The residue material 202 flowing out through the residue openings 204 is collected and discarded. The air blown through air tube 182, in combination with die opening 185, creates the tubular form for extrudate 205.

Advantageously, the microwave extruder apparatus 180 of the present invention assures that the pressures on the molten polymer material within the extruder apparatus 180 are much lower than compared to those pressures normally present in conventional extrusion machines. In fact, the only pressure step occurs in the passage through the tip and die opening 184, which occurs through pressure buildup due to the polymer melt forced by the driving force (see arrow A in FIG. 11) to move through the narrow tip and die opening 184. The driving force is being generated by a suitable forcing mechanism such as a caterpillar-type driving belt (see drive 220 in FIG. 14), a drive ram (see ram 228 in FIG. 15), a linear servo motor (not shown) or similar drive means (not shown). A force sensor (not shown) mounted on such drive devices in a position able to register the force given to the feedstock stack 197, allows to exactly define and control the driving force, i.e. in force patterns and levels. The output rate (flow) and therefore the dimensions of the extruded tube 205 are directly related to this driving force and will follow the force pattern in time. Because of the visco-elasticity of the melted polymer in the tip and die combination 183, the overall extruder system will behave as a high-frequency cut-off filter, but due to the lower volume of molten polymer material compared to conventional extruders, one will get a much higher cut-off frequency. Further, the overall transition time of the heated polymer material in the extruder, i.e. the time during which it melts and then exits the die opening 184, is much less than that found with convention extrusion processes, since that transition is only taking place within extruder tip and tie combination 183. This has the significant advantage of leaving the physical properties of the respective polymers in feedstock disks 194, 196 relatively unchanged throughout the present extruding process.

In a manner similar as explained above relative to mold 24, one can use a quasi-optical mode of high frequency microwaves to generate the microwave energy field 198 within microwave extruder apparatus 180. More specifically, a microwave energy beam 206 from microwave source 207 can be focused (see FIG. 12) by means of appropriate HDPE lenses 208 and metal mirrors 210, so that the appropriate width microwave energy field 198 penetrates through the microwave-transparent extruder tip and die unit 183, to cause heating and melting of the polymers 194, 196 as they move through the microwave field 198. Further, through use of an optical sensor 212, the temperature of the polymer material 194, 196 within the microwave field 198 can be sensed. Then, through an appropriate feedback loop 214 and controller 215, the microwave source 207 can be quickly adjusted to enable precise control of the temperature within the microwave field 198 of the microwave extruder apparatus 180.

Thus, the microwave energy, as applied within the microwave field 198, can be changed fairly directly, and instantaneously, so it is possible to control the melting temperature of the polymer in disks 194, 196 within the microwave field almost instantaneously. This, in turn, makes it possible to combine different type polymers, i.e. with quite different melting temperatures, like the respective polymer disks 194, 196, as they move through the microwave field 198 within tip and die unit 183.

Further, there is a certain type of extrusion process known as "bump extrusion" used in forming angiography and other medical products. During a bump extrusion process, one changes the output of the polymer melt through the tip and die. This is done by either changing the conventional driving force, i.e. melt-pump or screw speed, directing the polymer melt into the extruder head causing a pressure change in the head, thereby causing a larger melt output. Alternatively, one can change the speed of the pulling caterpillar (see caterpillar drive unit 213 in FIG. 12), dragging the extrudate 205 and polymer melt out of the tip and die combination 183. However, due to the visco-elastic properties of the polymer melt and the large volume of melted polymer between the driving motors and the tip and die opening 185, as well as the large distance between the caterpillar drive 213 and tip and die 183, changing the output flow and by that in turn creating a bump, is a relatively slow process with conventional extruders. However, with the present invention, it is quite easy to change the push or drive force applied to stack 197 of polymer disks 194, 196, as further described below.

Also, if instead of using a so-called "bump" extrusion process, a so-called "rotating" extrusion process is desired, that alternate extrusion process can also be accomplished with the present invention, and at very high rotational frequencies. In essence, there are three parts elements with the microwave extruder 180 of the present invention that can be rotated independently, being the tip 184 mounted about the end of the air tube member 182, the die 192, and the stack 197 of polymer disks. By counter-rotating the tip 184 and the die 192, one can orient the molten polymer under an angle with the axis. By reducing the linespeed (i.e. the axial flow of the molten material through the tip and die 183) and keeping the rotational speed the same, one can achieve also a change in orientation angle. Further, there is now a new option available, which is not possible with conventional extruder heads. That is, one can now rotate the stack 197 of the polymer disks while leaving the tip 184 and die 192 stationary, or even counter-rotating the latter in relation to the disks. The net effect of rotating the stack of disks is an angular orientation of the middle polymer layer, were as both the inner as well as the outer boundary layer in contact with the tip 184 and die 192 surfaces are aligned with the axis.

Figure 13A:
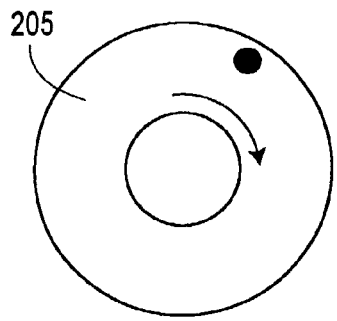
FIGS. 13a–d are end views of the polymer feedstock members, and the tip and die combination unit, as being rotated showing different angular orientations for the molten polymer resulting from rotating different extruder components.
Figure 13B:
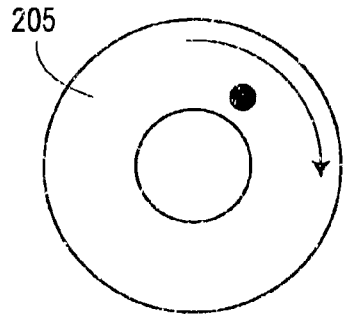
Figure 13C:
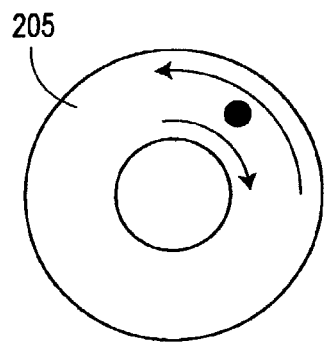
Figure 13D:
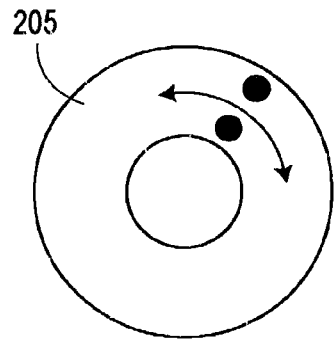

The above three options are represented in cross-section of the extruded tube 205 in FIGS. 13a–13d. It will be understood that the arrows in these Figures are pointing in the orientation of the polymer, while the dot means no orientation in angular direction. FIG. 13a describes the orientation of the inner layer of extrudate 205—by rotating the tip 184. It will be understood that, as previously noted, since the die tip 184 is rigidly mounted to the air tube 182, rotating the air tube will cause rotation of the die tip. Note that FIG. 13b reflects orientation of the outer extrudate layer by rotating the die 184. Next, FIG. 13c reflects the orientation resulting from counter-rotating the respective tip 184 and die 192. Finally, FIG. 13d reflects orientation of the layers when the disk stack 197 is being rotated.

Figure 13E:
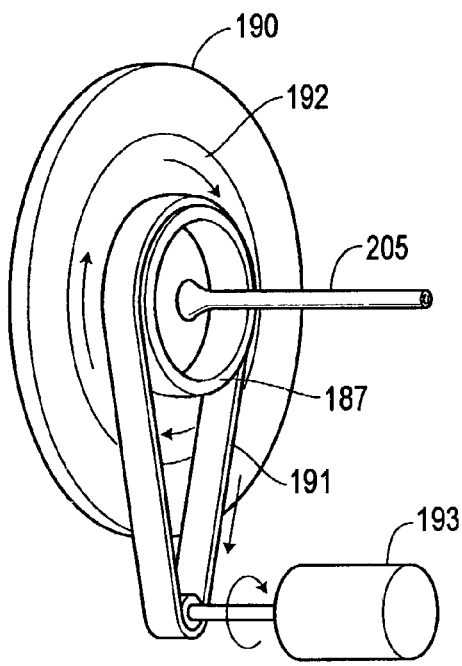
FIGS. 13e–g are views depicting different component rotational schemes for effecting angular orientation of the molten polymer.
Figure 13F:
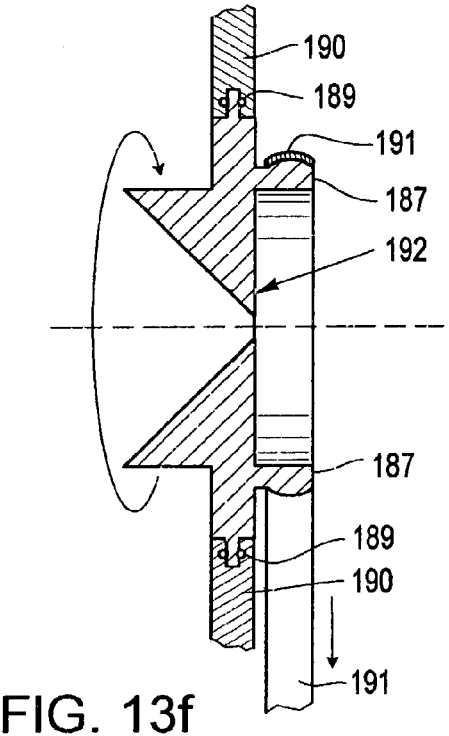

The rotation of the three above-noted elements can be accomplished as follows: since the tip 184 is connected at the rear to the air tube 182, which tube is running through the center of the stack 197 of the polymer disks, one can connect the air tube 182 to a motor (not shown) on the rear of the extruder head to allow spinning of the tip 184. If needed, one can add an enclosing non-rotational tube (not shown) around the air tube 182 at those places where the polymer disks 194, 196 are still solid, so as to prevent friction between the disks and the rotating shaft 182. However, having a motor (not shown) connected on the proximal side of the air tube 182 will make it difficult to feed unitary new disks into the stack 197 on the air tube. Also, even without a motor, it will be impossible to feed new disks into the air tube when the later is connected to some kind of air supply (not shown). However, this problem is overcome by cutting the disks into two halves, or molding them in that two part shape from the outset, if desired. Then, one can clip such disk halves 196a, 196a' (see FIG. 15) around the air tube 182 as a clamshell, to create the stack 197. Alternatively, see FIGS. 13e and 13f, the outer die 192 can be rotated quite easily by integrating an additional quartz drive ring 187 on the front (i.e. exterior) side of the die 192, and also by mounting a bearing 189 located outside of the microwave field 198, with the bearing 189 permitting rotation of die 192 relative to and by cooperating with the fixed die support wall 190. This allows the die 192 to be rotated by conventional ways such as via a drive belt 191 and drive motor 193, or via a drive gearwheel (not shown).

Figure 13G:
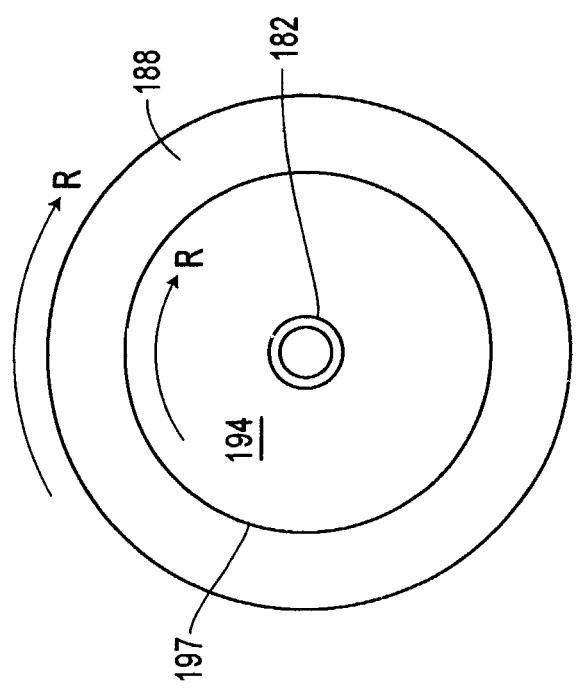

As seen, regardless of structure used, the present invention allows both the tip and die combination 183, as well as the incoming polymer disks 194, 196, to be easily rotated as desired, and all while the disks 194, 196 are pushed forward by a suitable forcing mechanism into the tip and die combination 183 at a very low speed. FIG. 13g shows an overall end elevation view (taken from the left end of extruder apparatus 180 in FIG. 12) showing the rotation of the disks 194, 196 and related tip and die parts, with that rotation occurring in the direction of arrows R. As explained, such rotation is quite easy with the present microwave extruder process, as compared to normal extrusion under conventional extruding processes, since the overall mass involved in such rotation is now quite low.

Depending upon the needs of the resultant extrudate for the end medical or angiography product being manufactured, the present invention also lends itself readily to use of multiple types of polymers, which can be combined and extruded in endless combinations. That is, instead of using two different polymer types, e.g. polymer feedstock disks 194, 196 of FIG. 11, three, four or even more different polymer types can be used for the feedstock disks. Further, instead of using polymer members formed in flat disk or ring section shapes, i.e. like polymer disks 194, 196 of FIG. 11, yet even different shapes for each of the different polymers can be used. For example, these can take the peripheral shape of pie sections, square or rectangular sections, and so forth. Further yet, polymer disks of different thicknesses can be used, i.e. where the second type polymer disk can be twice or more the thickness of the first type polymer disk.

Further, the present invention lends itself to the so-called "intermittent extrusion" process, because of the very small resultant transition zones present within the extruder apparatus 180. While such an "intermittent" extrusion process is explained in detail in U.S. Pat. No. 5,622,665, it will be understood that in a conventional intermittent extrusion process, one stops and starts two or more molten polymer streams into the extruder head. Starting and stopping melt pumps or valves just before the extruder head can, for example, accomplish this. The internal volume of the conventional extruder head is, however, rather large, and therefore take considerable time to empty the extruder head from one polymer and to switch over to the next polymer and then back again. Further, the smaller the extruded tube 205 is, the longer the transition zones between the two polymers being used. However, if one could make the transition zones very short, then one can alter the stiffness of an extended tube 205 very quickly along the axial direction. With the present invention, the transition zone in the microwave extruder head 183 is extremely small as the disks are only melted just before they leave the tip and die 183. That is, the volume within the head 183 where the molten polymers lie is much smaller than that of a conventional extruder head, and therefore, there is a much smaller transition zone.

Importantly, with the present invention, the overall dimensions of the extruder "head", i.e. the combination tip and die unit 183 in FIG. 11, is formed to be much smaller in both its overall diameter and in the resultant cross-sectional area for its volume of outflow (at tip opening 184), than can be achieved by the conventional extruder machine. This results from the fact that the overall extruding pressures are much lower in the tip and die combination 183 of the present invention than in conventional machines. A second reason is that the heating is not provided by the walls of the extruder, so there is no need for a large thermal mass.

When extruding so-called Pebax™ polymer material, it is well known that extruding at lower temperatures and therefore higher viscosities will result in higher strength angiography balloon products, primarily because of the axial orientation which occurs during the extrusion process of such material. However, the extremely high pressures found in conventional polymer extruding devices, due to the lower viscosities present, sets a definite process limit in this regard. Nevertheless, when Pebax™ material is used with the microwave extruder apparatus of the present invention, one need not be concerned with reaching too high of process pressures. Further, as explained above, the absence of shear forces and the reduced heat cycle adds the beneficial effect of less degradation of the Pebax™ material, as well as the fact that the material has a shorter transmission time in the microwave extruder apparatus 180. Thus, the microwave extruder apparatus of the present invention is well suited for use with such Pebax™ material.

Figure 14:
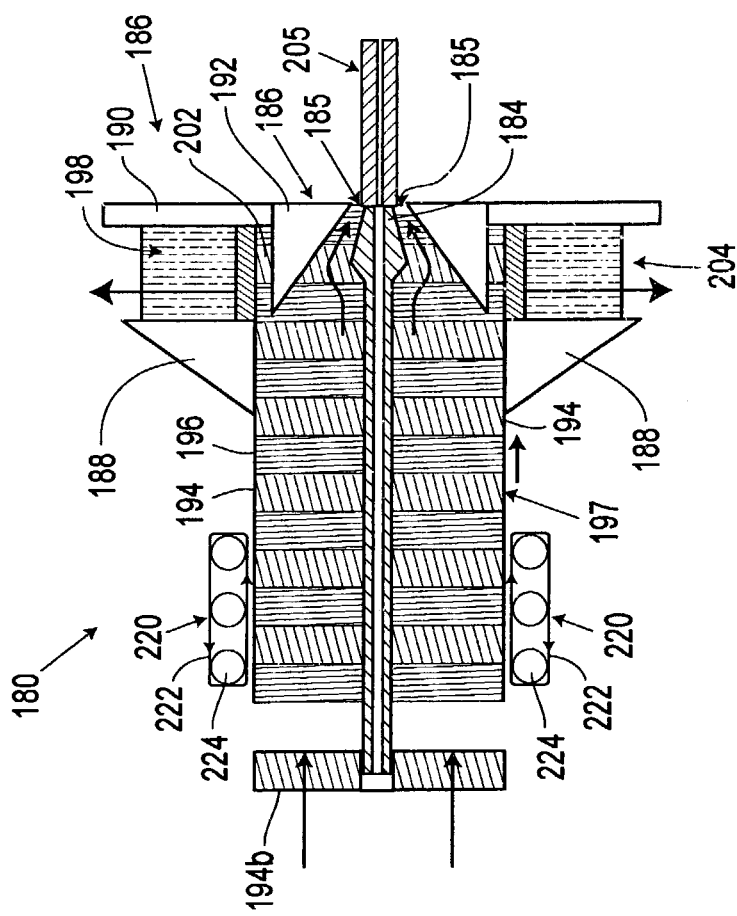
FIG. 14 shows the microwave extruder apparatus, with polymer feedstock members driven by a caterpillar drive mechanism.
Figure 15:
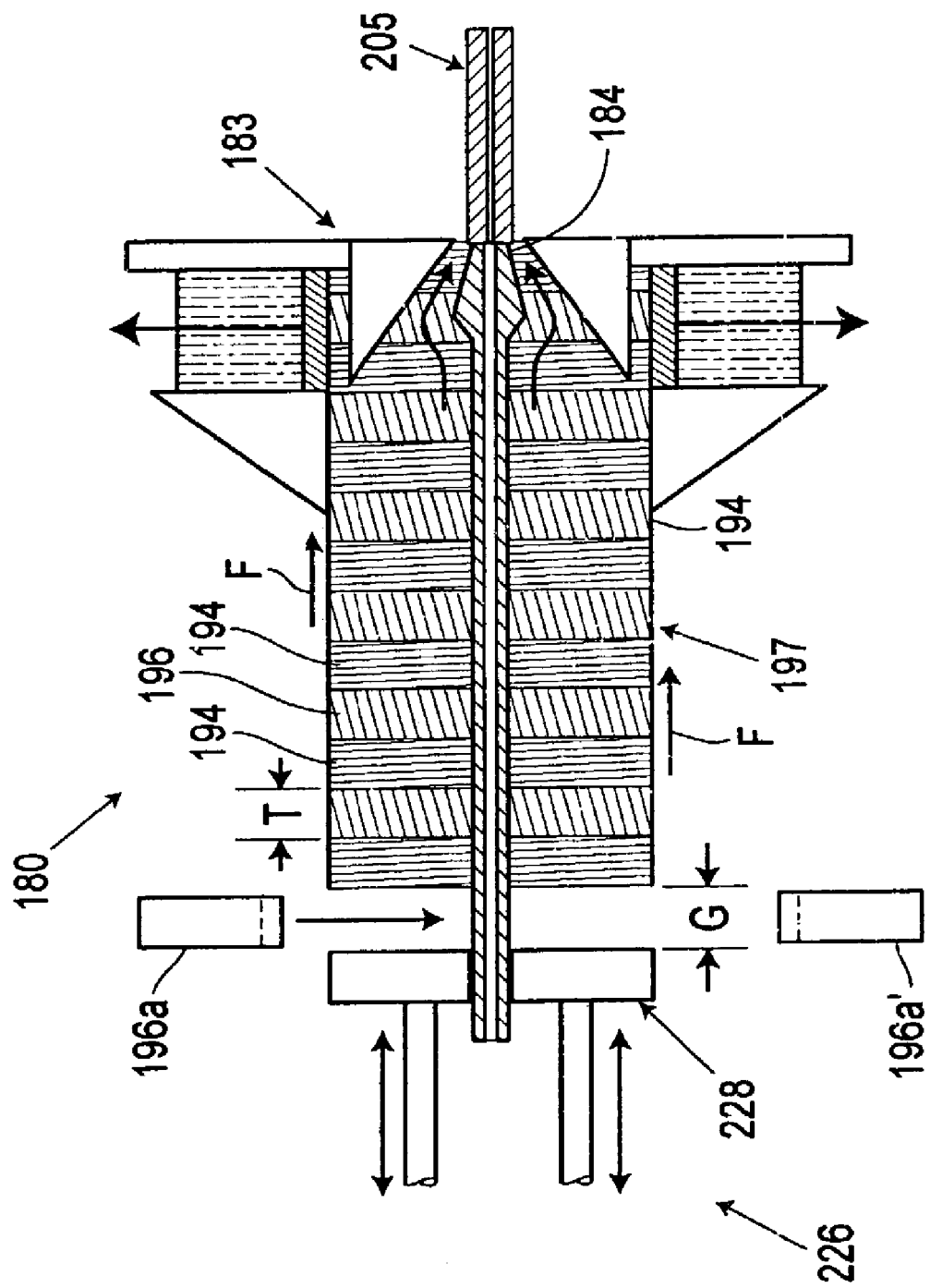
FIG. 15 depicts a servo-drive piston apparatus for the polymer feedstock stack.

Turning to FIG. 14, there is shown the microwave extruder apparatus 180 of the present invention, as modified for continuous operation. That is, in proper extrusion techniques for forming extrudates for use with balloon catheters and other medical and angiography products, the extruding operation should occur without interruption. Thus, there is a need to add the solid polymer disks 194, 196 in a continuous fashion, i.e. without interrupting the external push force of stack 197 to achieve such a continuous process. In one embodiment of this invention, this continuous operation is achieved by utilizing a forcing mechanism in the form of a gripping drive mechanism, generally denoted by reference numeral 218, on the side of the disks 194, 196. More particularly, this gripping mechanism 218 can take the form of a caterpillar drive mechanism 220. The caterpillar drive 220 includes a rotating drive belt 222, as driven by the rotating feed rollers 224, which cooperate to cause a continuous force to be applied to the outermost one (i.e. at the left end in FIG. 14) of the polymer disks 194, 196, so as to compress and drive the disk stack 197 towards the combination tip and die unit 183. Other known drive mechanisms, such as a rotating wheel drive (e.g. see FIG. 16n) can alternatively be used. In any event, the gripping mechanism 218 permits continuous feeding of new disks, e.g. regular insertion of new disks 194b (in FIG. 14) into the disk stack 197.

Such forcing or gripping drive mechanisms 218 can advantageously use the fact that the visco-elasticity of the molten polymer, e.g. material 194, 196 near the tip and die 183, is quite high. That is, an alternate continuous drive mechanism, generally depicted as gripping mechanism 226 in FIG. 15, comprises a servo-driven piston 228 that pushes the disk stack 197 a distance of the approximate thickness "T" of one disk 194. Then, after advancing that distance "T" in the forward direction towards tip and die 183, the servo piston 228 can be quickly retracted by the same distance "T", to allow sliding in sideways of a new disk 196 into the gap "G" that has now been created. Then, the piston 228 moves slightly to reestablish the forward driving force, in the direction of the arrows F in FIG. 15. By using servo motors (not shown), this advance, then quickly retract, then quickly re-advance operation of servo-drive piston 228 can be done quite precisely and fast. Further, any resultant "ripple" in pressure as noticed at the die opening 185 will be normally quite low due to the low speed and dampening present, which in turn are due to the higher visco-elasticity present in the molten polymer material 194, 196.

Figure 16A:
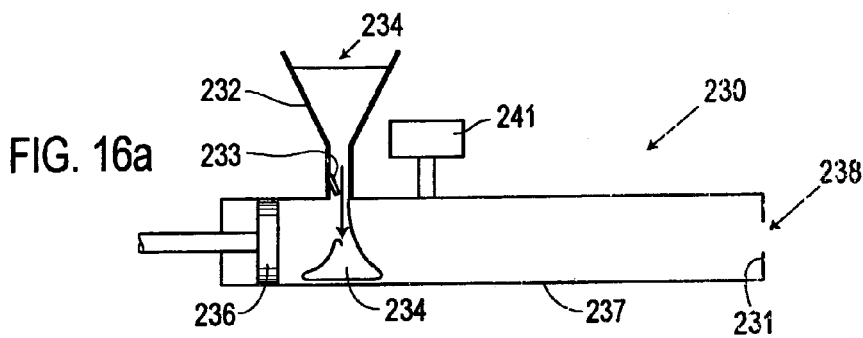
FIGS. 16a–h depict schematic representations of various operational stages of a polymer feedstock member-producing apparatus, and related components.
Figure 16B:
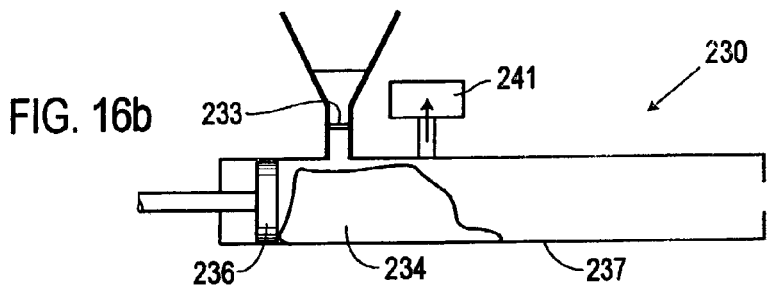
Figure 16C:
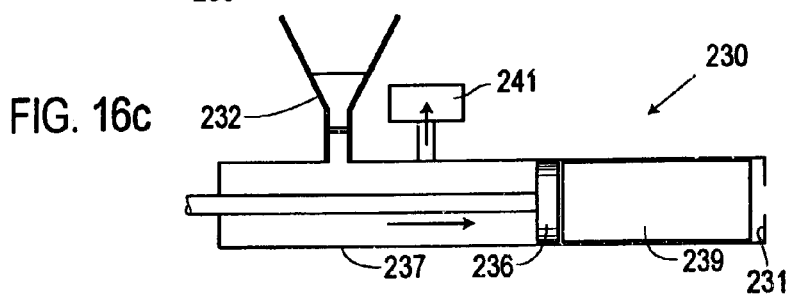
Figure 16D:
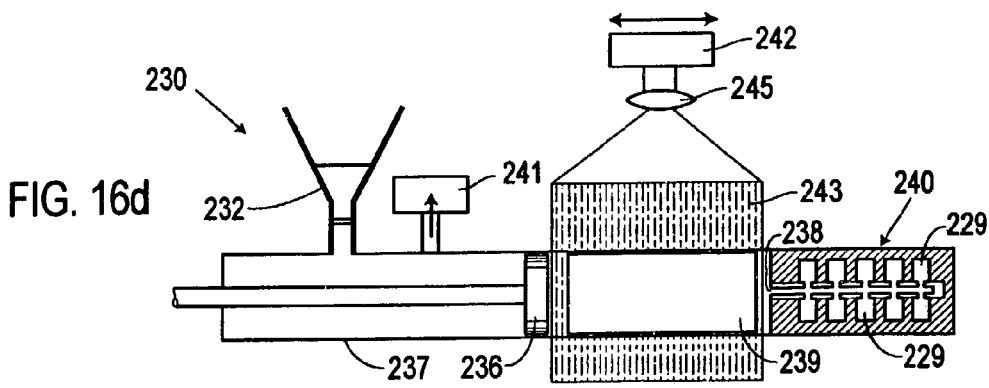
Figure 16E:
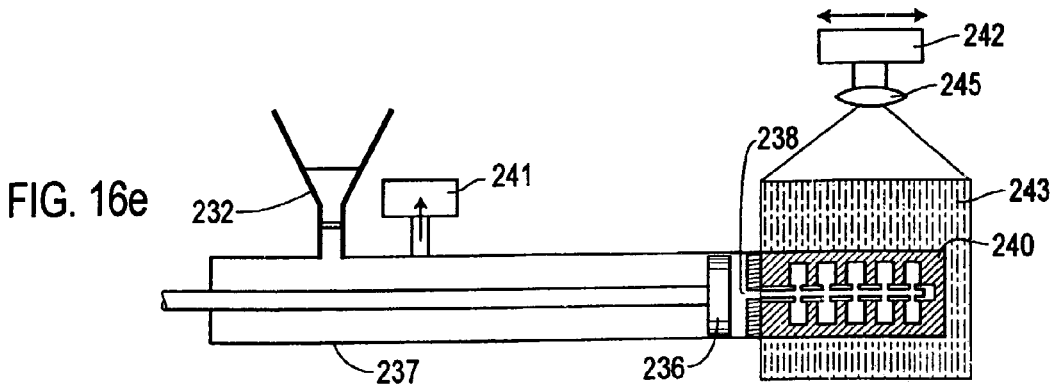
Figure 16F:
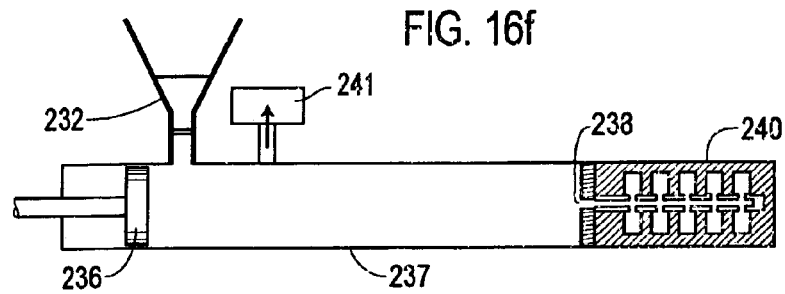
Figure 16G:
Figure 16H:
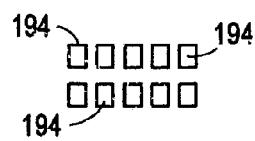
Figure 16I:
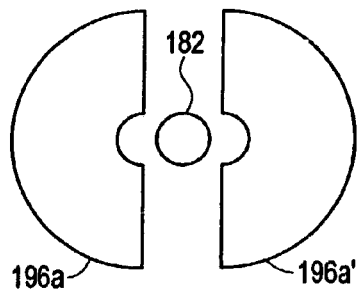
FIGS. 16i–n depict different polymer feedstock member designs, and related rotational configurations.

Turning to FIGS. 16a–16h, there is schematically shown a polymer feedstock member-producing apparatus, generally denoted by reference numeral 230 (see FIG. 16a). Apparatus 230 comprises a hopper 232 filled with polymer pellets material 234, feeds through a hopper door 233 to a barrel 237 having a forcing mechanism in the form of a force piston 236 and a feed opening 238. Once the hopper door 233 is closed (see FIG. 16b), a vacuum pump 241 is used to remove air from the barrel 237. The piston 236 is moved forward (to the right, see arrow, in FIG. 16c) compressing the pellets 234 into a pellet block 239 against end wall 231. An appropriate microwave energy source 242 producing a microwave energy field 243 through a focusing lens 245 is then used as the heat source to melt the pellet material 234 within the barrel 237, as shown in FIG. 16d, prior to entry into the disk mold 240. Then, the piston 236 continues to push the now molten pellet block material 239 through the opening 238, into a disk mold 240 having individual disk-shaped cavities 229, to create the uniform-shaped polymer rings or disks, e.g. disk 194. Note that the microwave source 242 and lens 245 can be made to move (to the right between FIGS. 16d and 16e), so as to present the microwave field 243 across mold 240 and the molten polymer now forced therein, to help maintain the molten state of the latter until the mold 240 is fully filled in. Once that has occurred (see FIG. 16f), the microwave field 243 is turned off, and the molded parts are cooled and then removed from the mold 240, to result in a "tree" 243 (see FIG. 16g) of individual polymer disks 194, 196, which can be broken off into separate disk elements (see FIG. 16h). That process is then repeated, by retracting piston 236 and microwave source 242 (back to left in FIG. 16a), and repeating the above process steps, to make yet another group of such new polymer feedstock disk members 194, 196.

As described above, relative and similar to mold 24 and also extruder tip and die 183, the piston 236 and barrel 237 of apparatus 230, as well as mold 240, all can be made out of a suitable Quartz, glass, Teflon, or other microwave-transparent material, thus allowing the external microwave energy field 243 to penetrate through such material and heat and melt the polymer material.

It will be understood that the piston 236 and barrel 237 themselves can alternatively be formed out of a metallic material; then the piston 236 and barrel 237 will become a wave guide. In that case, homogeneous heating within the barrel 237 can be obtained by using a variable frequency microwave. That is, by means of sweeping through a frequency range for the microwave heat source 242, one could generate many different wave modes over time, which on average create a homogeneous distribution of the microwave energy in the barrel. This is referred to as "electronic mode stirring".

When combined with the microwave extruder apparatus 180 of FIG. 11, this microwave heating with the polymer disk-producing apparatus 230 (for forming polymer pellets into polymer feedstock disks) assures that one can go from polymer pellet material 234 to feedstock disks 194, 196, and then from those disks to the end tubular extrudate product 205. And this is all done with the assurance that there is a very short overall combined microwave-created heating time of the polymer material. Thus, the present invention has great advantages in minimizing degradation of the various polymer materials used, both in the pellet-melting and in the microwave extruding process.

Figure 17A:
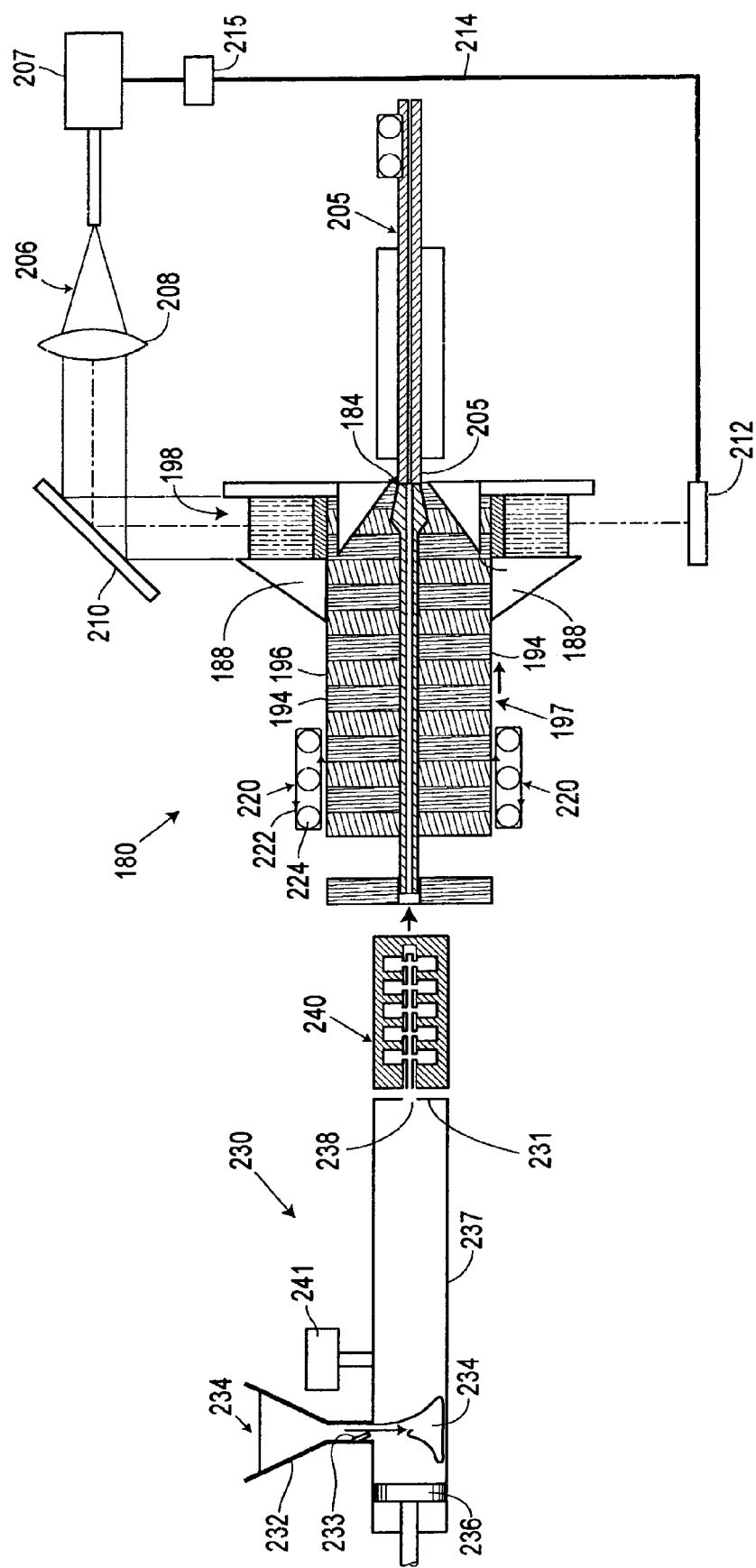
FIG. 17a is a schematic representation of the overall pellet-to-polymer disk-to-disk stack-to-microwave extrusion process in accordance with the teachings of the disclosure.

The overall microwave polymer melting, disk-forming, and microwave extrusion process is shown in partial block diagram format, in FIG. 17a, where the polymer disks are created from microwave melting of polymer pellet material, via the polymer disk-producing apparatus 230, and then the disks so formed are transferred as polymer feedstock through the disk stack 197 to be melted via microwave in the microwave extruder apparatus 180, to be extruded into the polymer tube extrudate product 205.

Figure 17B:
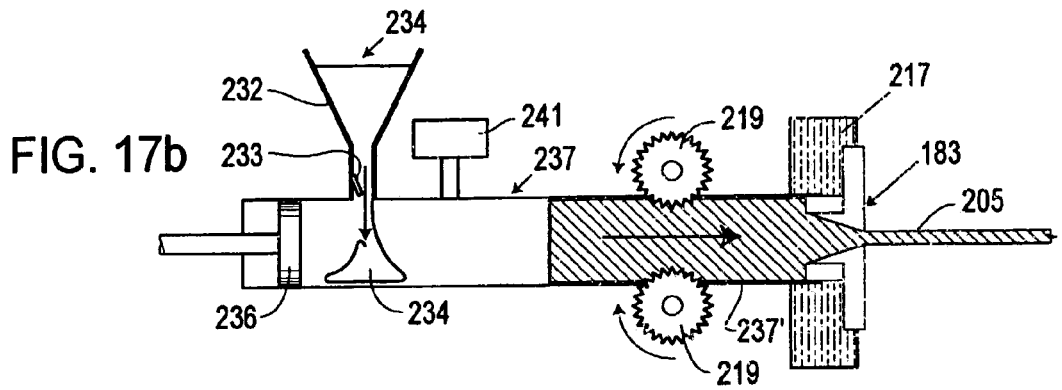
FIGS. 17b–17h are schematic representations of a modified pellet-to-molten polymer feedstock-to-microwave extruder process in accordance with the teachings of the disclosure.

Alternatively, one could eliminate the disk-producing apparatus 230, which creates polymer disks 194, 196 from the polymer pellet material 234. Instead, as shown in FIGS. 17b–17h, one could go directly from microwave melting of the pellets 234 to the microwave extruder apparatus 180, with the addition of a barrel extension 237 around the molten polymer feedstock material to contain it after it leaves the barrel 237, and while it slightly hardens and proceeds as a polymer tube to the cutting die section 192 of the microwave extruder apparatus 180. More specifically, this alternate approach is to first compress the pellets, and then melt them together with and into the last, i.e., tail end, section of the prior and now solid polymer feedstock as it is heading towards the extrusion head. In that way, one can control the polymer feedstock. That is, the solidified feedstock, as polymer tube 211, is driven continuously towards the extrusion head by means of a forcing mechanism in the form of rotating cog-wheels 219 that grip into the outer surface of the polymer tube 211. As seen in FIG. 17b, one can open the hopper 232 and fill the empty barrel 237 with pellets 234. The solidified polymer tube 211, i.e. from the just previous molten pellets and cycle, is driven forward to the extruder head through the presence of a continuous microwave field 217, by the series of rotating cog-wheels 219. The barrel extension 237' surrounding the polymer tube 211 has openings which allow the rotating cog-wheels 219 to each be in direct driving contact with the solidified polymer tube 211. The barrel extension '237 is also made from microwave-transparent materials (as previously described), so that the material within the extension 237' can be heated via a suitable microwave field.

Figure 17C:
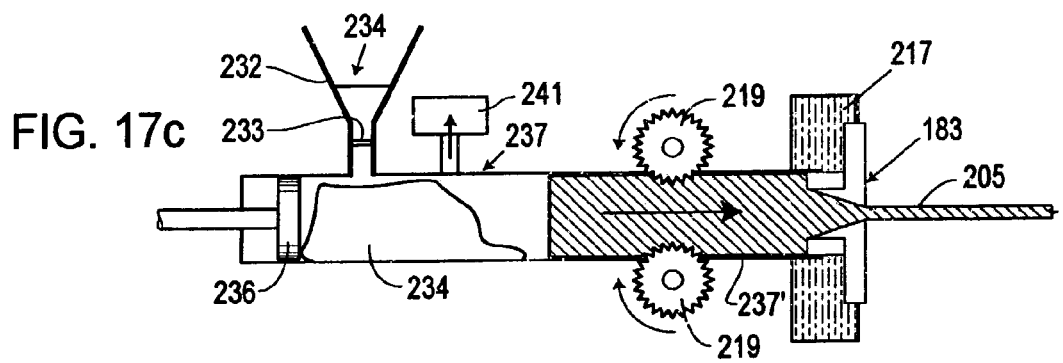
Figure 17D:
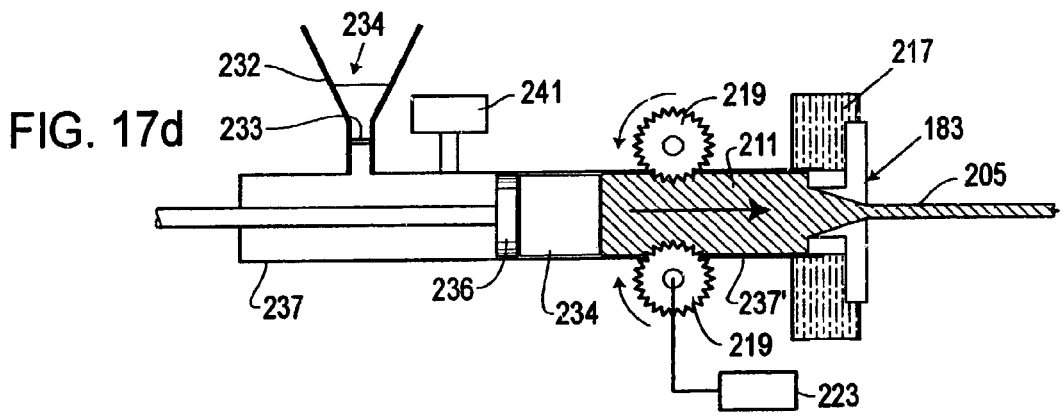
Figure 17E:
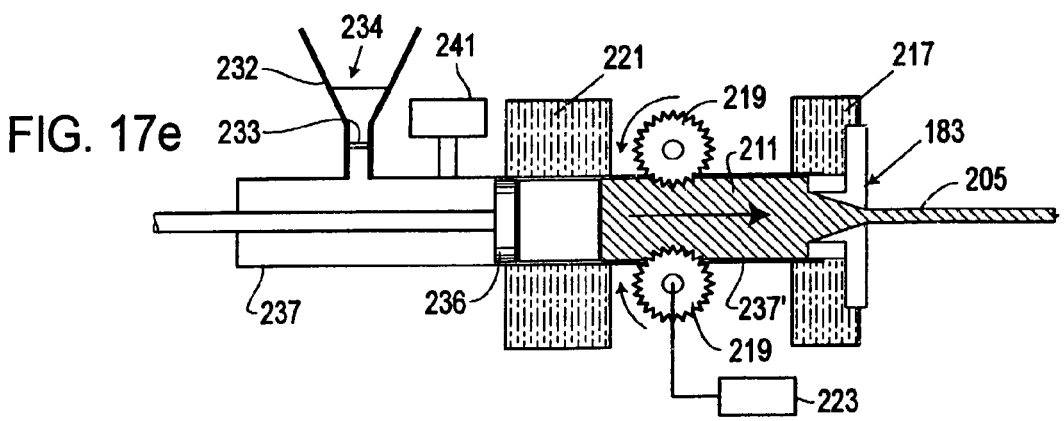

Then, as seen in FIG. 17c, the hopper lid to barrel 237 is closed, and a vacuum is created within the barrel 237 by means of vacuum pump 241. Then, as seen in FIG. 17d, the piston 236 is moved forward to compress the pellets 234 against the solidified polymer tube 211 downstream in the barrel extension 237'. Next, as depicted in FIG. 17e, one turns on a second microwave field 221, which melts the pellets 234 in the barrel 237. The microwave field 221, due to its extra width, will also melt the last or tail end section of the just formed polymer tube 211. This assures that the molten pellets 234 in barrel 237 become a part of the solidified tube 211 after they also have solidified. During the melting process, one pushes the piston 236 continuously (i.e. to the right in FIG. 17e) to make sure that all voids disappear in the polymer melt 234. The rotating cog-wheels 219 will counteract this forward pushing force (i.e. of piston 237) to make sure that the overall force of polymer tube 211, as seen inside the extrusion head, remains constant. Thus, preferably, a torque sensor 223 is attached to the cog-wheels 219 to create a stable pressure in the extrusion head. One could, of course, instead use a microwave-transparent fiber pressure sensor (not shown) in the extrusion head to measure the internal extrusion pressure.

Figure 17F:
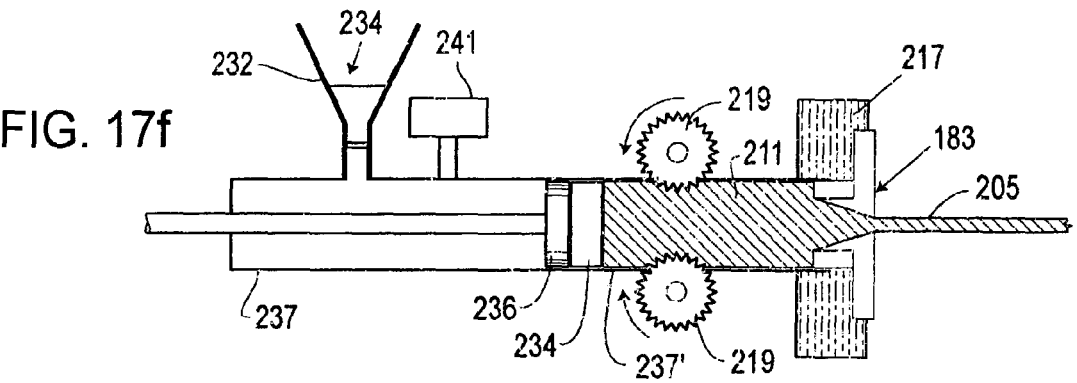
Figure 17G:
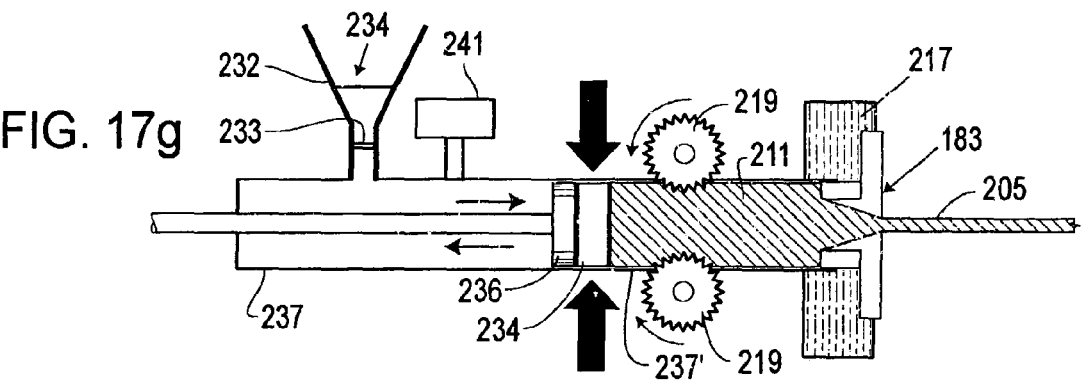
Figure 17H:
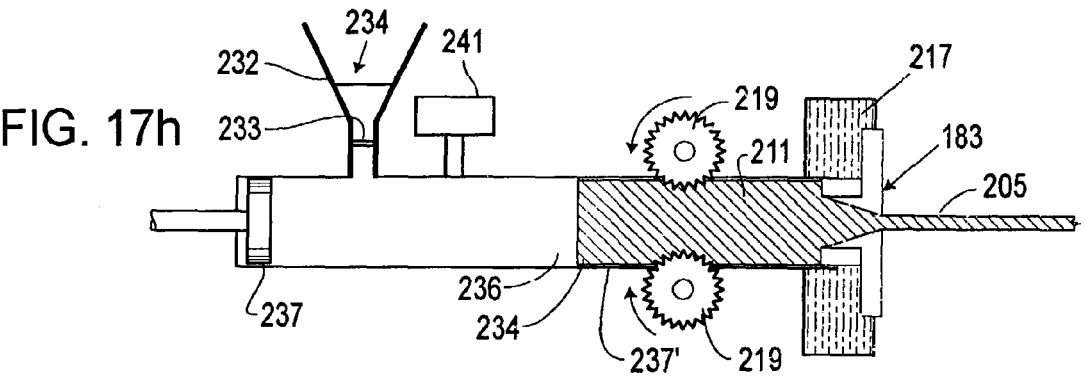

Then, see FIG. 17f, one turns off the second microwave field 221, and advances the piston 236 further and pushes the molten polymer 234 into a compressed tube shape, which is now connected to the left slightly molten tail end of solidified tube 211. Next, see FIG. 17g, one cools the polymer melt 234 with prior solidified tube 211, while maintaining the forward drive of the piston 236. This cooling process can be made even faster by active cooling, for example, by using a forced cooled-air flow (see vertical arrows in FIG. 17g) to cool the barrel extension 237'. Alternatively, one could make the piston 236 hollow (not shown) and flush it with a coolant during this particular cooling step. Then, as seen in FIG. 17h, once the newest rear end addition to the polymer tube 211 is cooled, the piston 236 is retracted (to its left position in this FIGURE), to repeat the above process steps.

The reason for cooling down the molten polymer stream 234, into a resolidified tube 211, is to have that polymer remelt act, in effect, like the solid disk stack 197. In this way, as the solid disk stack enters the combination tip and die area 183 and is melted by the microwave field 198, it has a viscosity much higher (not unlike the disk stack 197) than the viscosity of the molten polymer flow within the microwave field 198 and the tip and die 183. This, in turn, accomplishes several things, i.e. it prevents any unwanted backflow of molten material around cutter die 192, and it also lets enough pressure to build up in solid polymer tube 211 to force out the molten polymer flow within the tip and die 183 to form the extrudate 205.

Figure 17I:
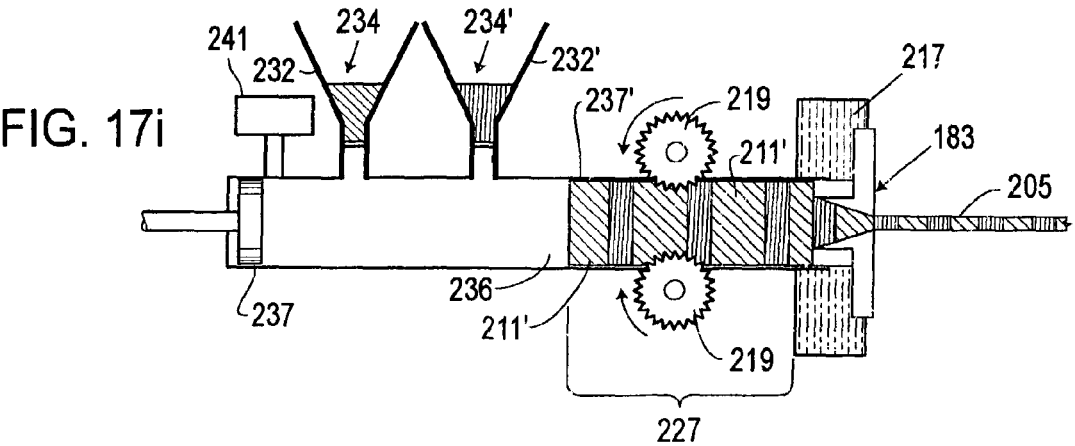
FIG. 17i is a schematic representation of a further modification to the modified process of FIGS. 17b–17h.

As yet a further modified embodiment, there is shown in FIG. 17i a direct pellet melter-to-microwave extruder apparatus and process, similar to that as shown and described above as to FIGS. 17b through 17h, but modified to have a second pellet hopper 232' intended to receive a second type polymer pellet material 234'. This modified embodiment can be used with two different and alternately-melted polymer pellet types 234, 234'. In operation, it creates a modified solidified tube 211' having an intermittent polymer pattern 227, which can be advantageously used for special extrudate product applications, as desired.

Figure 18A:
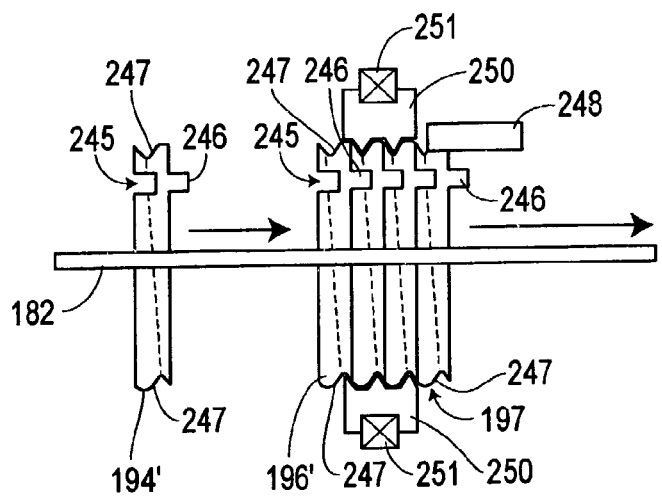
FIGS. 18a–d depict a rotating-type drive apparatus for use with the polymer disks in accordance with the teachings of the disclosure.
Figure 18B:
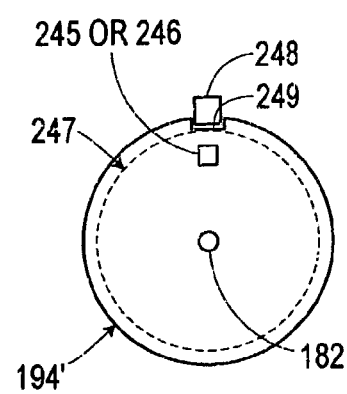

Seen in FIG. 18a is a rotating drive apparatus, generally denoted by reference numeral 244, as used for continuously forcing connected feedstock members 194, 196 into the microwave extruder apparatus 180. More specifically, rotating drive apparatus 244 utilizes modified disks 194', 196' that have on one side a female receiving opening 245 and directly on the other side a protruding or male drive tab 246. Preferably, see FIG. 18b, the mating and corresponding receiving opening 245 and drive tab 246 are square-shaped (although they can be round, triangular or of other suitable shape, as desired). As will be appreciated, the respective driving tab 246 on a given disk member 194', when cooperatively engaged into the receiving opening 245 on a mating, next adjacent disk member 196', together create a locking mechanism to cause the disk stack 197 to move, and separately to rotate about support rod 182, as an integral unit. Further, the modified polymer disks 194', 196' of FIGS. 18a and 18b include a spiral groove 247 formed on the other periphery of each disk member 194', 196'. Also, as best seen in FIG. 18a, a running rail 248, as mounted adjacent to the rotating drive ring 250, is caused to sit within a corresponding U-shaped channel 249 formed transversely in the outer periphery of each disk member 194', 196'. Further, a rotating threaded drive member 250 affixed axially and supported by journal bearings 251 is threadedly engaged with the spiral drive threads or groove 247 of the respective disk members 194', 196'. In this fashion, it will be understood that rotation of the rotating drive ring 250 will force the locked stack 197 of disk members 194', 196' to move to the right (see arrow in FIG. 18a), thereby driving the locked and integral disk stack 197 towards the microwave extruder apparatus 182 (not shown in FIG. 18a). The respective locking members 245, 246 are formed at the time the respective disk members 194', 196' are formed, as is the U-shaped channel 249. As will be understood, each new disk 194', 196', when introduced onto support rod 182, have its drive tab 246 locked into the exposed drive opening 245 of the next prior disk, to then become a locked part of the integral feedstock stack 197. As will be appreciated, both the locking members 245, 246, the spiral groove 247, and the U-shaped channel 249 of each of the feedstock disks 194', 196' are then cut off as they enter the cut-off dies 188 of the microwave extruder apparatus 180. In sum, this consecutive feed apparatus 244 allows a convenient way of feeding new feedstock disks to the feedstock stack, and on into the microwave extruder apparatus, all without interrupting the continuous flow of the feedstock stack 197.

Figure 18C:
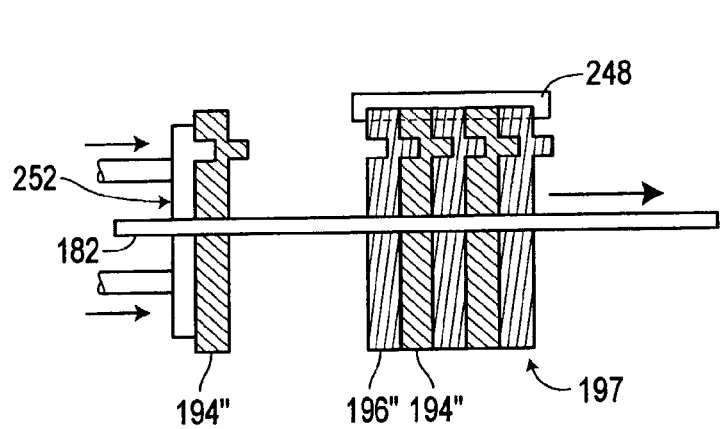
Figure 18D:
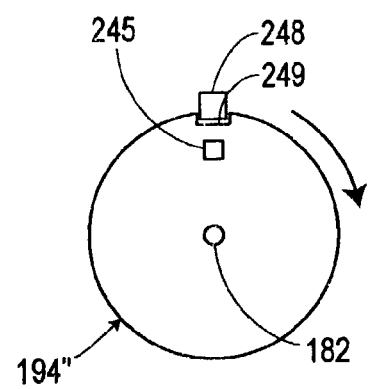

As seen in FIG. 18c, the respective disks 194', 196' can also be moved towards extruder 180 in an alternate manner. That is, instead of having spiraling grooves 247 and a rotating drive ring apparatus, the axial running rail 248 is caused to be rotated (see arrow in FIG. 18d), which due to its engagement in the U-shaped grooves 249 of the respective polymer disks 194", 196", causes such disks to similarly rotate. Then, under the driving force of a driving ram, generally denoted by reference numeral 252 (see FIG. 18c), the connected stack of disks 197 is caused to move forward towards the microwave extruder apparatus 180. Thus, using a servo drive system (not shown), one can stop and start the rotation of the rail 248, and thus the resultant rotation of the disk stack 197, for a very short time, to enable feeding of yet a new disk 194" onto the rear of the stack. Preferably, there is a feeding of a large number of such disks, so as to minimize any effects from the stopping and starting of the continuous flow of polymer feedstock via rotating and moving disk stack 197 towards the extruder apparatus. Thus, this rotating rail 248 is seen as yet one additional way of rotating the disks, depending on the overall desired output qualities for the extrudate product 205.

Figure 16J:
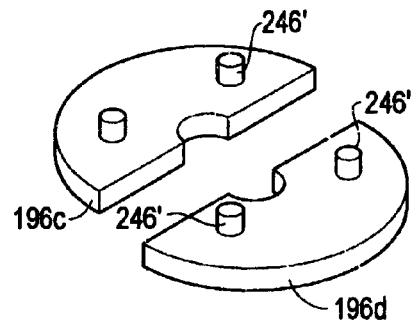
Figure 16K:
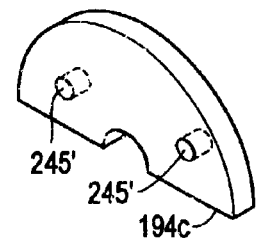
Figure 16L:
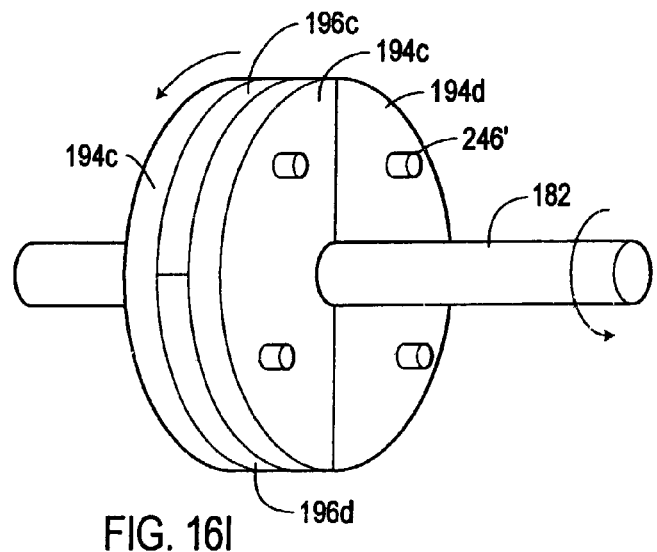

As seen in FIG. 16j, there is shown yet another form of a two-part disk, as formed of disk halves 196c, 196d. These disks 196c, 196d are slightly modified from disks 194', 196' of FIGS. 18a and 18b, in that these disk halves 196c, 196d each have at least two protruding nubs 246' on their front faces, and corresponding receiving openings 245' (not shown) on their rear faces. FIG. 16k shows the back face of one half (of two halves) of a modified disk 194c, also formed with projecting nubs 246' (not shown), and receiving openings 245'. Thus, as seen in FIG. 16l, the respective disk halves 194c, 194d, and 196c, 196d, are joined together about the rotating air support tube 182, via interconnection of their respective receiving openings 245' and locking nubs 246'. As seen, here again in FIG. 16l, pairs of disk halves 194c, 194d, and 196c, 196d can be repetitively mounted onto the air support tube 182, and rotated (via auxiliary means, not shown) to move the modified disk stack 197' towards the microwave extruder apparatus, and to create desired angularity characteristics for the extrudate 205.

Figure 16M:
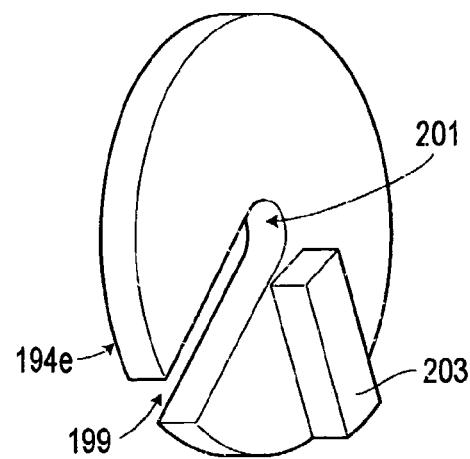
Figure 16N:
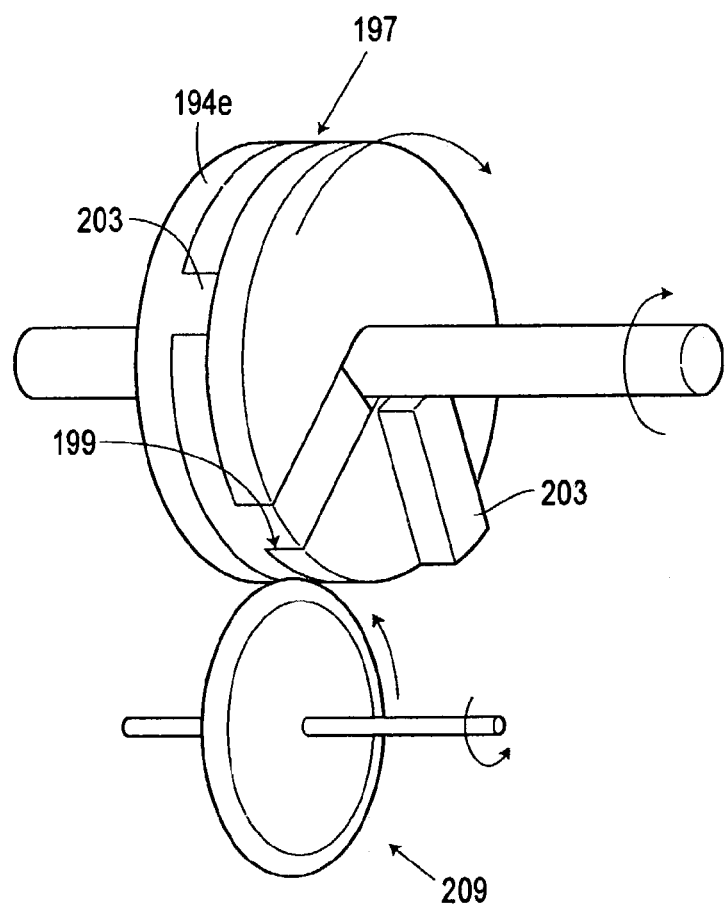

Further yet, in FIG. 16m is shown a modified one-piece disk 194e as having a thru-slot 199 formed from the outer peripheral edge of the disk to the inner central opening 201, and a corresponding outwardly-raised, radially-aligned filler bar 203. Filler bar 203, when the modified disk 194e is mounted on the air support tube 182, acts to fill the void left by the insertion thru slot 199, on the next adjacent modified disk 194e. In that fashion, a solid disk stack can be created, without any voids (since the filler bar 203 of one disk completes and fills in the void in the next adjacent disk 194e, as well as creates an interconnection therebetween), so that the disk stack is not only integral and void-free, but can be rotated (via auxiliary drive wheel 209 see FIG. 16n). Thus, FIG. 16n reflects yet another way of creating an integral drive stack, which can be rotated towards the microwave extruder apparatus (not shown in FIG. 16n), and to create desired angularity.

Figure 19:
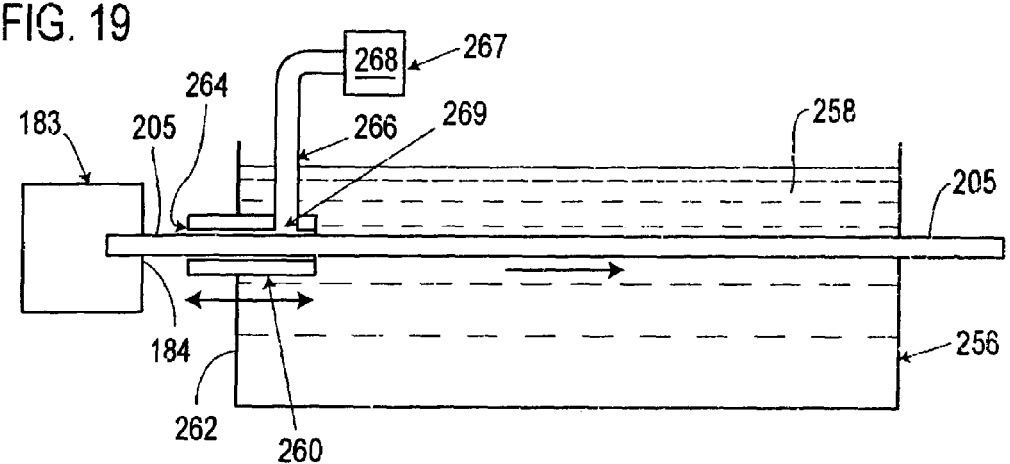
FIG. 19 depicts a cooling tube apparatus for the extrudate in accordance with the teachings of the disclosure.

There must be proper cooling of the polymer extrudate products, such as the extrudate tube product 205, after it leaves the extruder die opening 184. However, there is an increasing need to realize a fast cooling of the extruded tube to fix the orientation of the polymer chains. Thus, FIG. 19 depicts the use of one embodiment of an improved cooling apparatus, generally denoted by reference numeral 254, of the present invention. More specifically, as described above, the extruder tip and die head 183 is used to extrude the polymer materials into the extruded tubular product 205. That extrudate 205 is then quickly cooled to achieve the desired uniform size and material characteristics for use in angiography and other medical products. To do this, the cooling apparatus 254 initially can comprise a cooling bath tank 256 holding a cooling bath liquid 258. The cooling bath liquid 258 can be formed of, for example, water. The cooling apparatus 254 can further comprise a cooling pipe member 260 that is fitted to the left end wall 262 of the cooling tank 256. In operation, the extruded tubular product 205 is caused to flow through the proximal opening 264 of the cooling pipe 260. Additionally, an inlet pipe 266, connected to a supply 267 of an appropriate cooling medium 268, is fitted to the cooling pipe 260 through an inlet opening 269. Suitable material for cooling medium 268 can include hydrogen, helium, and air. Even chilled water can be suitable for the cooling medium 268. The hydrogen, helium and air can also be cooled.

In operation, the cooling pipe apparatus 260 causes the cooling medium 268 pumped therethrough to constantly flow across the just-extruded polymer tube product 205, which extrudate product is moving (left-to-right in FIG. 19 through the cooling pipe 260 and then into the cooling tank 256).

Figure 20:
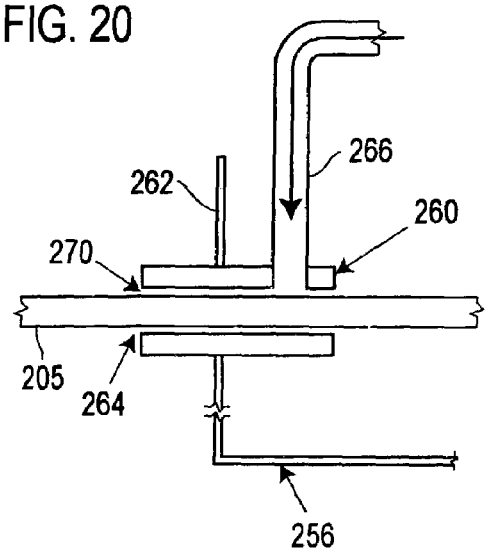
FIG. 20 is an enlarged view of the cooling tube of FIG. 19, and showing additional cooling structure.

As seen in FIG. 20, which is an enlarged cross sectional view of the cooling tube 260 and extrudate 205 of FIG. 19, there is a small gap, denoted generally by reference numeral 270, present between the outer diameter of the extruded polymer tube 205 and the internal diameter of the silver tube 260. The gap 270 can be no greater than, for example, $3.10^{-4}$ m. It is within that gap 270 that the cooling gas 268 (or alternately, cooling water) travels and works to cool the outer surface of the tubular extrudate 205.

Silver material is preferably used for the cooling tube 260, since it has a very high thermal conductivity, i.e. being some 616 times higher than that of water. Further, since it is impossible to have the moving tubular extrudate 205 be in direct contact with the silver tube 260, a highly conductive cooling medium, i.e. the cooling gas 268, is used in the gap 270 between the silver tube 260 and the extruded tube product 205. Instead of a silver material, a copper or a tungsten material, or a mixture of any or all three, can be used for forming tube 260. Also, since water would turn to steam, it is preferable to use a cooling gas medium, such as helium gas, hydrogen gas or air. Helium gas has a five times higher thermal conductivity than air, while hydrogen gas has a 6.7 times higher thermal conductivity than air.

Figure 21:
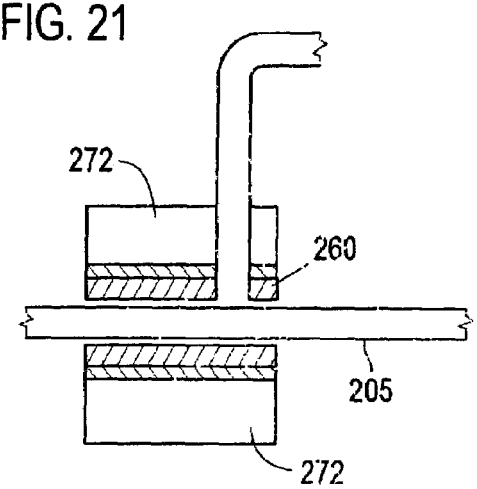
FIG. 21 depicts a modification of the cooling tube apparatus of FIG. 19, and a cooling tank apparatus.
Figure 21A:
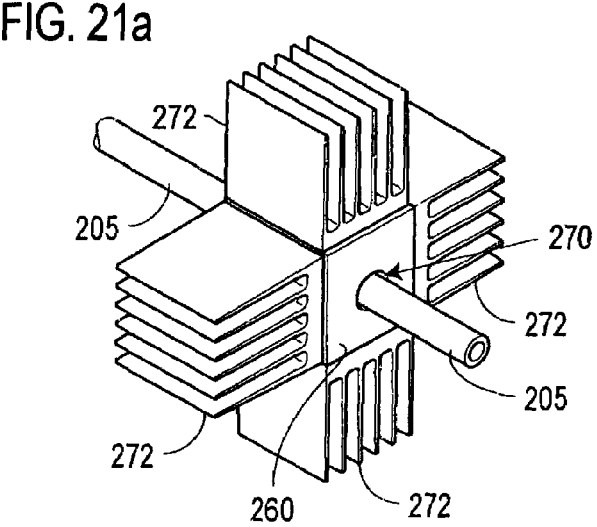
FIG. 21a depicts a further modification of the cooling tube apparatus of FIG. 19.

The silver tube 260 can be modified as shown in FIG. 21, by not only being submersed within the water bath of tank 256 (not shown in this Figure), but also by having cooling fins 272 attached to its outside surface. The fins 272 assure, due to the extremely high heat conductivity of the silver material, that the silver tube 260 remains at a uniform temperature, i.e. being generally equal to the water temperature in the cooling bath 256. In fact, cooling the water to near 0° C. is even possible. An even better cooling can be obtained by mounting so-called peltier elements 273 on the outside of the tube 260 and the cooling fins 272 (See FIG. 21a). Such peltier elements (which provide thermo electric cooling) are able to generate a large temperature difference (of 50° C. or even more) relative to an outside basis, for example, to a water basin at room temperature (not shown). Therefore, by maintaining the hot-side of the peltier elements 273 at room temperature, such as by blowing air through the cooling fins of the peltier elements 273, one can drive the cold-side of the peltier element 273, as attached via gluing or other means, to the silver tube 260, to −30° C., i.e. well below room temperature.

In one example made in accordance with the present invention, the extruded tube 205 exits the microwave extruder apparatus 180 at approximately 180° C. and then directly enters the silver tube 260. Hydrogen gas 268 is blown at a relatively low speed through the annular space or gap 270 between the silver tube 260 and the extruded tube 265. Note, there is relatively little danger for explosion if using hydrogen gas, as only very low volumes of such gas are even needed.

There are multiple ways of utilizing the silver tube 260 to affect rapid cooling of the extruded tube product 205. In one embodiment of the invention, air is used as the cooling gas 268. This affects the efficiency of the overall cooling system 254 in that it goes down by a factor of 7, as compared to using hydrogen gas instead. That is, by blocking the hydrogen input, and instead switching to air as the conducting or cooling gas 268 through inlet pipe 266, one can make a substantial change (here an increase) in the needed cooling distance quite rapidly, i.e. that is, the distance it takes for the extruded tube 205 to be cooled to the ambient temperature. On the other hand, when using water as the conducting cooling medium, i.e. instead of hydrogen or helium gas, a yet quicker cooling can be established by a factor of 2.8.

Figure 22:
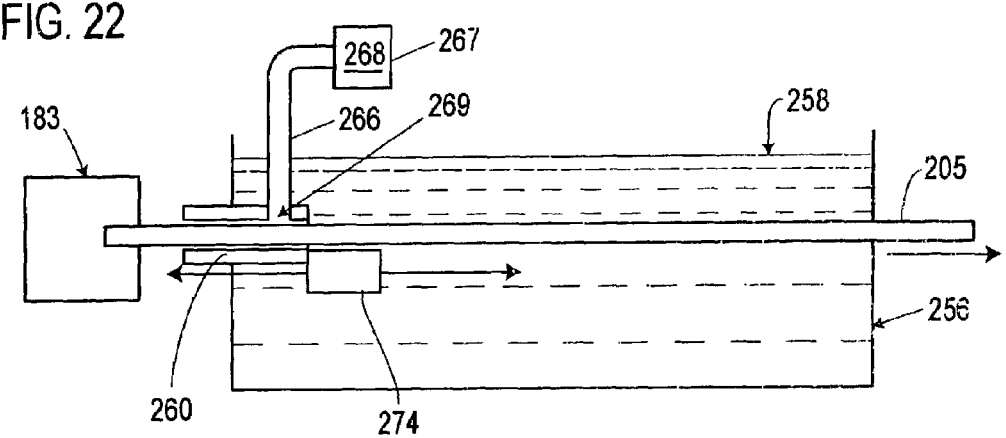
FIG. 22 depicts a modification of the cooling tube apparatus of FIG. 19.

Further, as seen in FIG. 22, the silver cooling tube 260 can be modified so that, instead of being stationery, it can move in an axial (left to right horizontal, in FIG. 22) direction along the extruded polymer tube 205 quite rapidly. This can be achieved, through the use of the pipe drive motor 274, which can move the silver cooling tube 260 back and forth axially (see arrow in FIG. 22) along the extruded tube product 205.

Figure 23:
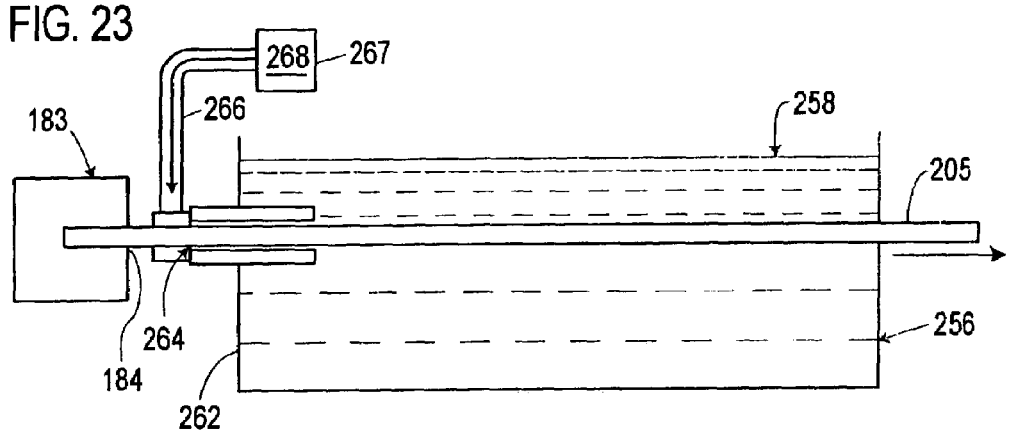
FIG. 23 depicts another modification of the cooling tube apparatus of FIG. 19.

Finally, as seen in FIG. 23, the silver cooling tube 260 can be constructed so that, instead of having the conducting/cooling gas 268 blown from within the cooling bath 258, the conducting gas 268 is blown in from the other side, i.e. the left end of the silver tube 260 (see left side in FIG. 21) and nearest to the extruder die opening 184, through proximal opening 264. This is done by closing the gap or volume otherwise present between the extruder tip and die head 183 and the left end wall 262 (FIG. 19) of the cooling bath 256.

Figure 24:
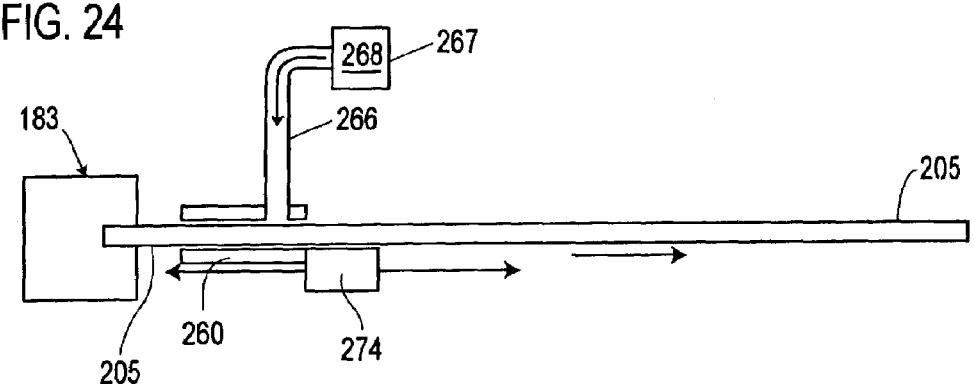
FIG. 24 depicts a modified cooling tube, without any related cooling bath structure.

Overall, the goal of using a silver cooling tube 260, whether as used in the embodiment of FIGS. 19, 21, 21a, or 23, is to help reduce the overall length of the cooling bath 256. That is, the additional cooling provided to the tubular polymer extrudate 205 by way of the silver cooling tube 260 helps reduce the amount of additional cooling to be provided to the extrudate by the cooling bath 256, such that the length of the latter can be reduced. Further, it will be understood that, by using the silver cooling tube 260, in conjunction with a high concentration of cooling medium 268 (whether it be a cooling gas, or air), one can even eliminate the overall use of the cooling water in a cooling bath 256. That, in turn, is advantageous, as it causes elimination of the need for common dryer blowers (not shown) used to remove the film of cooling water from the extruded tube 205, once the latter has been cooled. For example, there is shown in FIG. 24 the use of the cooling tube 260, as directly receiving the extrudate 205 from the microwave extruder head 180, and all without use of any additional cooling bath structure or medium.

Figure 25:
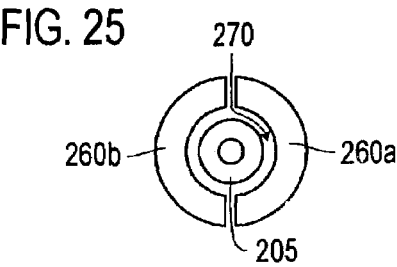
FIG. 25 depicts a modified cooling tube with split tube structure.

It will also be understood that, no matter which of the above cooling approaches is utilized, the silver cooling tube 260 can be formed of a split-tube design. That is, as seen in cross section in FIG. 25, tube 260 can be split in half, along its axial direction, i.e. into two tube halves 260a, 260b. Such a split-tube design has the advantages first, of allowing the easy placement of silver cooling tube 260 around the extrudate 205 after the extrusion process has started, and second, of allowing the silver cooling tube 260, depending on the separation set between halves 260a, 260b, to accommodate extrudate 205 of different dimensions. That is, tube halves 260a, 260b can be separated just enough to leave a narrow gap 270 between them and the exrudate 205.

It will be understood that, if needed for extruded polymer processing reasons, then the above-described microwave heating, with or without a mold, of a portion of the extruded tube product 205, so as to create the balloon portions 34, can be readily undertaken and accomplished right in line with the formation of the extruded polymer tube product 205 itself.

Based on the foregoing, one of ordinary skill in the art will readily understand that the teachings of this disclosure can be employed to create an apparatus and method for effectively and quickly forming polymer disks, and then extruding such polymers using microwave energy, and for cooling such extruded polymer products.

What is claimed is:

1. A method of manufacturing medical devices, comprising:

providing a stack of alternating polymer disks of at least two different polymers, the disks each having an axial hole therein for accommodating an air tube, the air tube comprising a distal end that forms an open die tip, the open die tip being disposed within a cutter die, the cutter die comprising an outer tip disposed upstream of the open die tip and an inner tip in alignment with the open die tip that defines an annular space with the open die tip for accommodating extrudate, the cutter die being fabricated from microwave-transparent material, moving the stack of disks over the tube and towards the annular space, heating the stack of disks disposed between the outer tip of the cutter die and the open die tip with focused microwave energy, whereby the polymer disks are melted just prior to exiting the annular space as extrudate.

2. The method of claim 1, wherein the microwave energy is generated by one of a gyrotron and a magnetron.

3. The method of claim 1, wherein the cutter die is formed of one of Quartz material, ceramic material, glass material, Teflon® material, boron nitride material, and mixtures thereof.

4. The method of claim 1, further comprising cutting off an outer peripheral edge of the stack of polymer disks with the inner tip of the cutter die.

5. The method of claim 4, wherein the cutting off of the feedstock material occurs after the heating with focused microwave energy.

6. The method of claim 1, wherein the moving the stack of disks comprises applying a drive force to the stack.

7. The method of claim 6, wherein the applying of the drive force comprises applying a force along an outer edge of the stack.

8. The method of claim 6, wherein the applying of the drive force comprises a force applied to the stack at the end thereof opposite the cutter die and open die tip.

9. The method of claim 8, further comprising intermittently ceasing applying the drive force to the stack, thereby to allow introduction of additional polymer disks over the tube.

10. The method of claim 6, wherein a caterpillar drive device is used to apply the drive force.

11. The method of claim 8, wherein a drive piston is used to apply the drive force.

12. The method of claim 1, further comprising rotating one of the cutter die or open die tip so as to create desired angularity characteristics within the melted polymers of the disks.

13. The method of claim 12, wherein the cutter die is disposed within an outer die, the method comprises rotating the outer die.

14. The method of claim 12, further comprising counter-rotating the open die tip and the cutter die.

15. The method of claim 13, further comprising counter-rotating the open die tip and the outer die.

16. The method of claim 1, further comprising continuously adding new separate polymer disks to the stack.

17. The method of claim 1, further comprising forming the polymer disks to have interconnection members, whereby rotation of a given separate polymer disk will cause rotation of the stack.

18. The method of claim 17, wherein the interconnection members comprise one of a male tab and mating female opening.

19. The method of claim 1, wherein each of the polymer disks are formed as two mating halves.

20. The method of claim 11, further comprising causing the drive piston to advance the stack by a distance of the thickness of one separate polymer disk, retracting the drive piston by the same thickness distance, inserting a new separate polymer disk between the piston and stack, and re-advancing the drive piston to repeat the cycle.

21. The method of claim 1, further comprising forming a spiral groove in an outer periphery of each separate disk, and causing rotation of the stack by rotating a drive ring against the spiral groove of each respective disk.

22. The method of claim 1, further comprising providing a running rail through a peripheral notch formed in each disk-to assist forward driving movement of the stack towards the cutter die.

23. The method of claim 1, further comprising providing a running rail through a peripheral notch formed in each disk, and rotating the running rail to cause rotation of the stack into the annular space.

24. A method forming an extruded polymer medical device, comprising:

filling a supply hopper with a first polymer feedstock material;

transporting the first polymer feedstock material to a microwave-transparent barrel member;

removing air from the barrel member;

compressing the first polymer feedstock material;

applying microwave energy to the barrel member to melt the compressed first polymer feedstock material within the barrel member;

compressing the melted first polymer feedstock material against and into the end of a previously-formed and cooled tube of alternating second and first polymer feedstock materials, to add a new layer of first feedstock material to the tube;

filling the supply hopper with a second polymer feedstock material;

transporting the second polymer feedstock material to the microwave-transparent barrel member;

removing air from the barrel member;

compressing the second polymer feedstock material;

applying microwave energy to the barrel member to melt the compressed second polymer feedstock material within the barrel member;

compressing the melted second polymer feedstock material against the previously-formed layer of first feedstock material to add a new layer of second feedstock material to the tube;

forcing the tube of alternating layers of first and second polymer materials into a microwave-transparent extrusion tip and die; and applying focused microwave energy to the tube of alternating layers of first and second polymer materials inside the extrusion tip and die to melt the tube at a point just prior to being forced out of the extrusion tip and die to be formed into a polymer medical device.

25. The method of claim 24, further comprising cutting off an outer peripheral edge of the cooled tube of polymer feedstock materials as residue material proximate where the tube enters the extrusion tip and die.

26. The method of claim 24, wherein the step of forcing the cooled tube of polymer material comprises engaging rotating gear drive wheels with the peripheral surface of the tube to forcibly move the tube into the extrusion tip and die.

27. The method of claim 24 wherein the extrusion tip and die comprise an air tube which is accommodated in a central axial hole extending through the stack, the air tube terminating in an open die tip that is centrally disposed within a cutter die, the open die tip and cutter die defining an annular space through which extrudate moves.

* * * * *